United States Patent
Wu

(10) Patent No.: US 8,384,905 B2
(45) Date of Patent: Feb. 26, 2013

(54) TUNABLE LIGHT SOURCE FOR LABEL-INDEPENDENT OPTICAL READER

(75) Inventor: Qi Wu, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 308 days.

(21) Appl. No.: 12/939,606

(22) Filed: Nov. 4, 2010

(65) Prior Publication Data

US 2011/0109909 A1    May 12, 2011

Related U.S. Application Data

(60) Provisional application No. 61/259,802, filed on Nov. 10, 2009, provisional application No. 61/390,826, filed on Oct. 7, 2010.

(51) Int. Cl.
*G01N 21/55* (2006.01)
*F21V 11/00* (2006.01)

(52) U.S. Cl. ........ 356/445; 356/448; 356/218; 362/293; 385/12

(58) Field of Classification Search .......... 356/445–448, 356/218, 73; 362/235, 19, 293; 385/12; 436/164, 172
See application file for complete search history.

(56) References Cited

U.S. PATENT DOCUMENTS

| | | | |
|---|---|---|---|
| 6,429,022 B1 * | 8/2002 | Kunz et al. ................... 436/164 |
| 7,497,992 B2 | 3/2009 | Cunningham et al. ..... 422/82.05 |
| 7,599,055 B2 | 10/2009 | Gollier et al. ................ 356/246 |
| 2004/0130723 A1 | 7/2004 | Yager et al. .................... 356/445 |
| 2006/0180750 A1 | 8/2006 | Gollier et al. ............ 250/227.11 |
| 2008/0158570 A1 * | 7/2008 | Gollier et al. ................ 356/521 |
| 2008/0187011 A1 | 8/2008 | Kiesel et al. ................... 372/19 |
| 2009/0011948 A1 | 1/2009 | Unlu et al. ....................... 506/9 |
| 2009/0097013 A1 * | 4/2009 | Modavis et al. ............... 356/73 |
| 2011/0102799 A1 * | 5/2011 | Matejka et al. ............... 356/448 |
| 2011/0116095 A1 * | 5/2011 | Krol et al. ..................... 356/445 |
| 2011/0199607 A1 * | 8/2011 | Kanellopoulos et al. .... 356/73.1 |
| 2011/0238382 A1 * | 9/2011 | Gollier et al. ................. 702/191 |

OTHER PUBLICATIONS

Wiki, M., et al., "Wavelength-interrogated optical sensor for biochemical applications", Optics Letter, Apr. 1, 2000, vol. 25, No. 7, p. 463-465.
Wang, et al., "Theory and Applications of Guided-Mode Resonance Filters", Applied Optics, 32, No. 14, (1993), pp. 2606-2613.
Fang, et al., "Resnant Waveguide Grating Biosensor for Living Cell Sensing", Biophysical Journal, vol. 91, (Sep. 2006), pp. 1925-1940.

* cited by examiner

*Primary Examiner* — Hoa Pham
(74) *Attorney, Agent, or Firm* — John L. Haack

(57) ABSTRACT

A tunable light source for interrogating at least one resonant waveguide grating (RWG) biosensor having a resonance linewidth. The tunable light source includes a broadband light source that emits a light beam having a first spectral bandwidth greater than the RWG biosensor resonance linewidth. The broadband light source may be substantially spatially incoherent. A tunable optical filter having a tunable spectral linewidth is arranged to receive and filter the light beam to cause the light beam to have a second spectral bandwidth substantially the same as the RWG biosensor resonance linewidth. Label-independent optical readers that employ the tunable light source are also disclosed.

24 Claims, 16 Drawing Sheets

United States Patent US 8,384,905 B2

TUNABLE LIGHT SOURCE FOR LABEL-INDEPENDENT OPTICAL READER

CLAIM OF PRIORITY

This application claims the benefit of priority under 35 U.S.C. §119(e) of U.S. Provisional Application Ser. No. 61/259,802, filed on Nov. 10, 2009 and U.S. Provisional Application Ser. No. 61/390,826, filed on Oct. 7, 2010. The content of these documents and the entire disclosure of any publication or patent document mentioned herein is incorporated by reference.

FIELD

The present disclosure relates to a label-independent optical reader, and a light source for such a reader.

SUMMARY

In embodiments, the disclosure provides a tunable light source for interrogating at least one RWG biosensor having a resonance linewidth. The tunable light source includes a broadband light source that emits a light beam having a first spectral bandwidth greater than the RWG biosensor resonance linewidth. The tunable light source also includes a tunable optical filter having a tunable center wavelength. The tunable optical filter is arranged to receive and filter the light beam to cause the light beam to have a second spectral bandwidth substantially the same as the RWG biosensor resonance linewidth.

In embodiments, the disclosure provides a LID optical reader for reading at least one resonant RWG biosensor supported by a microplate. The optical reader includes the above-described tunable light source that emits a series of filtered light beams having wavelengths that sweep over the first spectral bandwidth. The optical reader also includes an illumination system to direct the series of filtered light beams to the at least one RWG biosensor and form a corresponding series of reflected light beams. The optical reader further includes an optical imager to receive the series of reflected light beams and form a corresponding series of digital images, and a controller to process the digital images to establish a resonant wavelength for the at least one RWG biosensor.

In embodiments, the disclosure provides a LID optical reader for reading at least one RWG biosensor supported by a microplate. The optical reader includes the above-described tunable light source that emits a filtered light beam having a fixed wavelength within the first spectral bandwidth. The optical reader also includes an illumination system to direct the filtered light beam to the at least one RWG biosensor to form a series of reflected light beams. The optical reader also has an optical imager to receive the series of reflected light beams and form therefrom digital images, and a controller to process the digital images to translate an intensity change to a resonant wavelength shift for the at least one RWG biosensor.

In embodiments, the disclosure provides a method of reading at least one RWG biosensor having a resonance linewidth. The method includes generating a light beam having a first spectral bandwidth greater than the RWG biosensor resonance linewidth. The method also includes passing the light beam through a tunable optical filter and adjusting the tunable filter to generate a series of light beams each having a second spectral bandwidth substantially the same as the RWG biosensor resonance linewidth but having different central wavelengths within the resonance linewidth. The method further includes directing the series of filtered light beams to be incident upon the at least one RWG biosensor and to generate a corresponding series of reflected light beams. The method additionally includes forming a series of digital images of the at least one RWG bionsensor based on the series of reflected light beams, and then processing the series of digital images to establish a resonant wavelength for the at least one RWG biosensor.

In embodiments, the disclosure provides a method of reading at least one RWG biosensor having a resonance linewidth. The method includes generating a light beam having a first spectral bandwidth greater than the RWG biosensor resonance linewidth. The method also includes passing the light beam through a tunable optical filter and adjusting the tunable filter to generate a light beam having a second spectral bandwidth substantially the same as the RWG biosensor resonance linewidth and a fixed central wavelength within the resonance linewidth. The method further includes directing the filtered light beam to be incident upon the at least one RWG biosensor to generate a corresponding reflected light beam. The method additionally includes forming a series of digital images of the at least one RWG bionsensor based on the reflected light beam, and then processing the series of digital images to establish a resonant wavelength for the at least one RWG biosensor.

BRIEF DESCRIPTION OF THE DRAWINGS

A more complete understanding of the present disclosure may be had by reference to the following detailed description when taken in conjunction with the accompanying drawings, wherein.

DETAILED DESCRIPTION

Label-independent detection (LID) based optical readers can be used, for example, to detect drug binding to a target molecule such as a protein, or changes in living cells as material is displaced within a cell in response to a drug. Certain types of LID optical readers measure changes in refractive index on the surface of a resonant waveguide grating (RWG) biosensor for an array of RWG biosensors. The individual RWG biosensors are located in respective wells of a microplate.

In one type of LID optical reader, spectrally broadband light from a light source is directed to each RWG biosensor. Only light whose wavelength is resonant with the RWG biosensor is strongly reflected. This reflected light is collected and spectrally analyzed to determine the resonant wavelength, with shifts in wavelength being representative of refractive index changes from biomolecular binding to the RWG biosensor, or similarly representing material displacements within cells immobilized to the sensor surface.

In another type of LID optical reader, narrowband light swept over a range of wavelengths is directed to each RWG biosensor using a narrow-band tunable light source. To date such tunable light sources have been limited to tunable lasers. Commercially available tunable lasers suitable for biosensor interrogations are primarily external cavity semiconductor lasers with tuning technologies based on grating cavities that produce an extremely narrow linewidth, and acousto optic tunable filters (AOTF) that generate a moderately narrow linewidth of about 50 pm. Although external cavity semiconductor tunable lasers have been demonstrated as viable light sources for LID optical readers, their relatively high cost limits their use. Vertical cavity surface-emitting lasers (VCSELs) provide a lower-cost option, but their optical power and tuning range is not sufficient for interrogating a full microplate.

Reference is now made to embodiments of the disclosure, exemplary embodiments of which are illustrated in the accompanying drawings.

Figure 1:
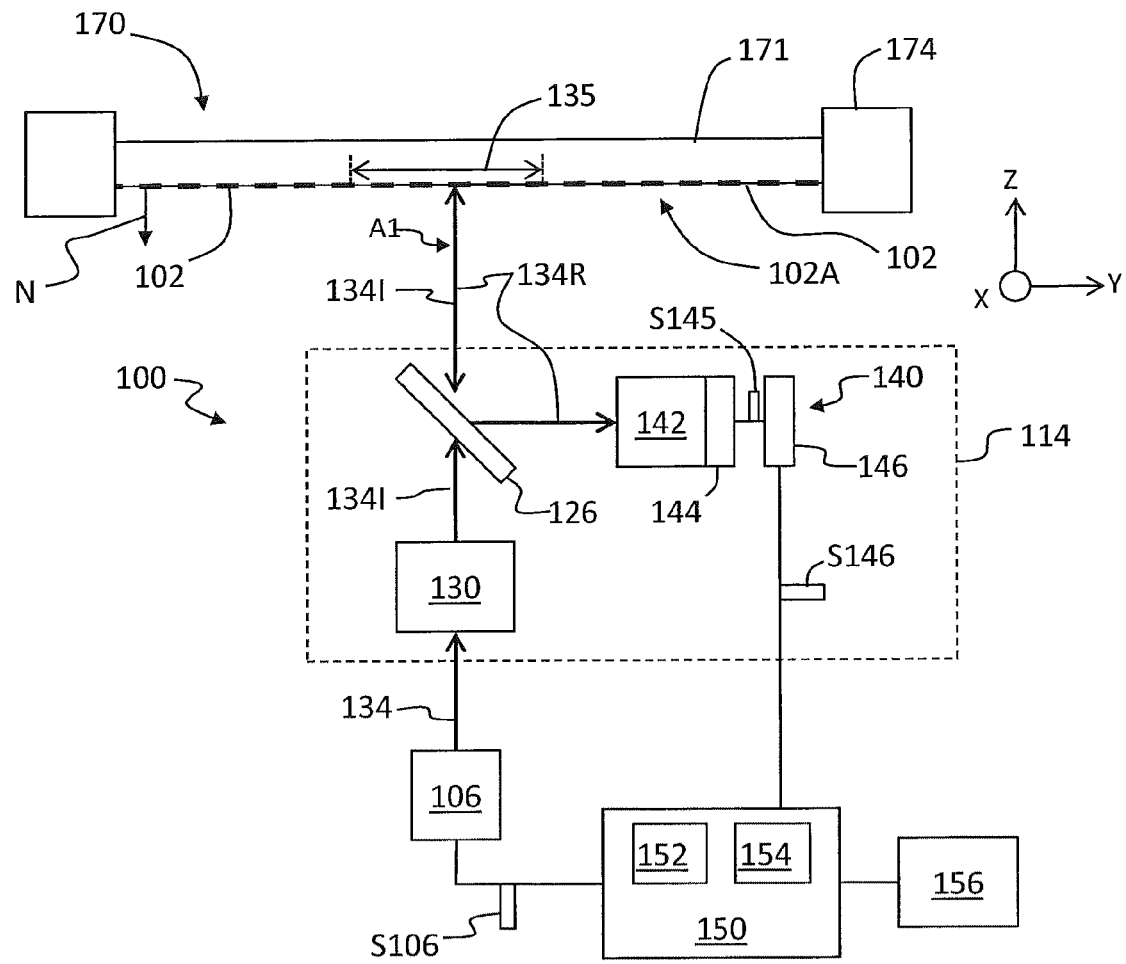
FIG. 1 is a generalized schematic diagram of an example optical reader system suitable for use with the tunable light source of the disclosure.

FIG. 1 is a generalized schematic diagram of an example optical reader system ("system") 100 suitable for use with the tunable light source disclosed herein. System 100 includes an imaging system 114 used to interrogate one or more resonant waveguide grating (RWG) biosensors 102. Imaging system 114 includes an illumination optical system 130 and an imaging optical system ("optical imager") 140. Example imaging systems 114 are discussed in greater detail below.

Figure 2:
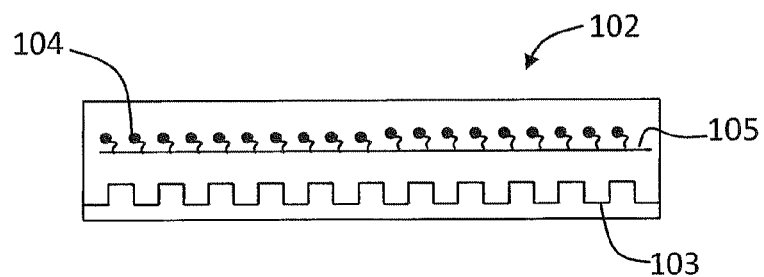
FIG. 2 is a close-up schematic view of an example RWG biosensor.
Figure 3:
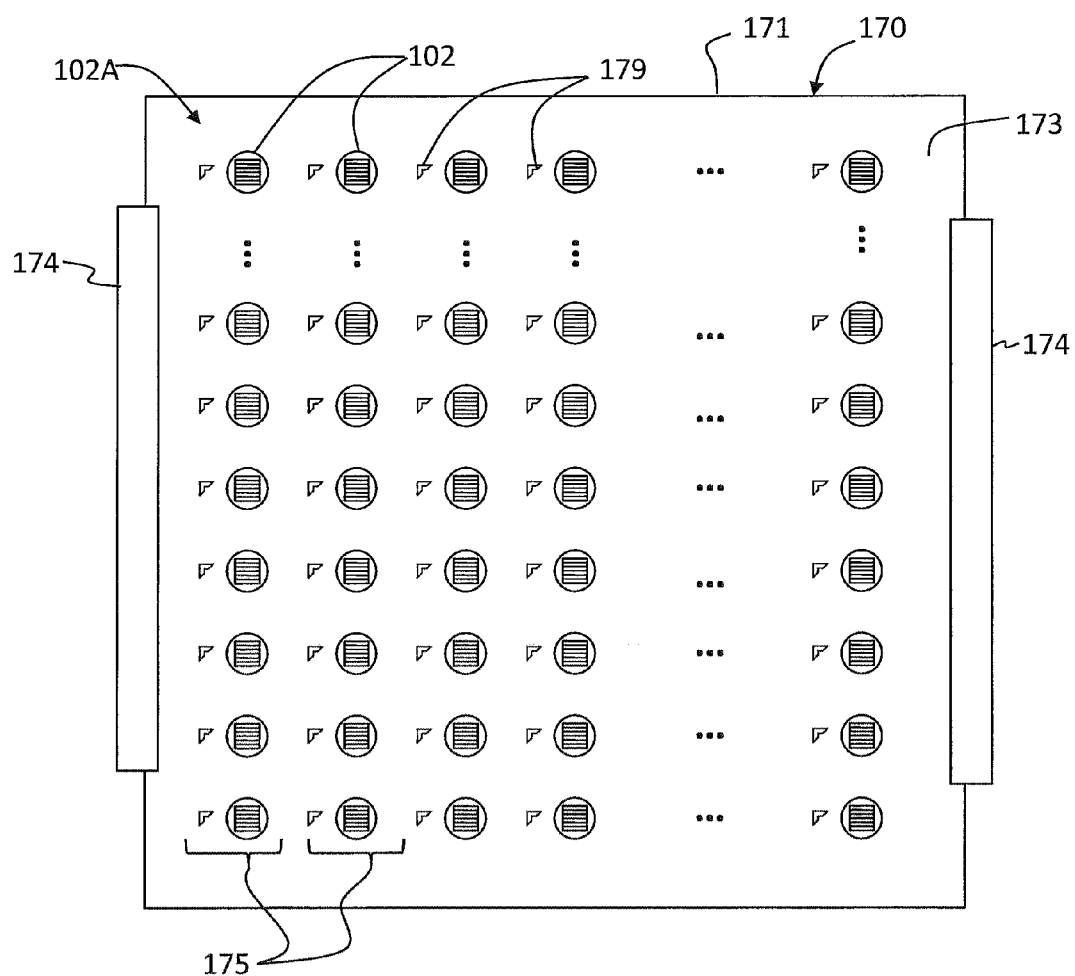
FIG. 3 is a face-on view of an example microplate that operably supports an array of RWG biosensors in associated regions or "wells," with the microplate being held by a microplate holder.
Figure 4:
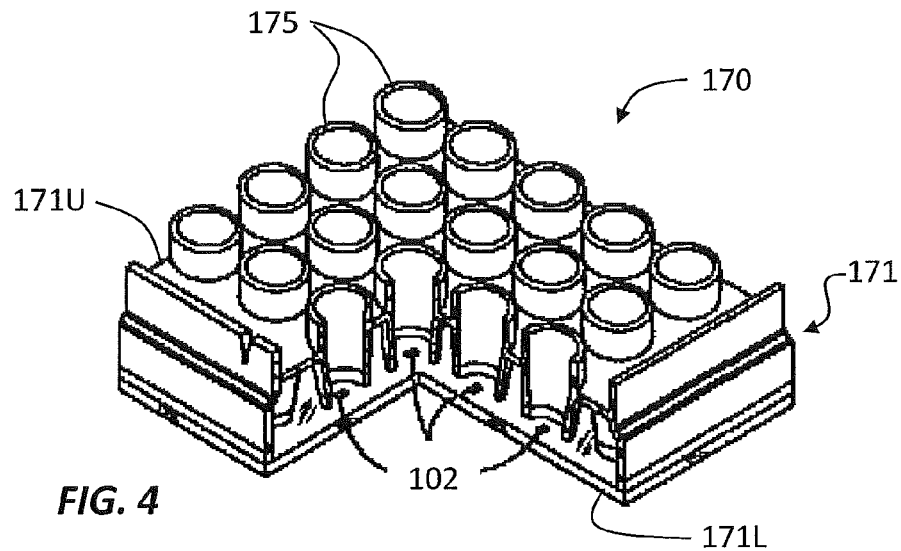
FIG. 4 is a cut-away perspective view of a portion of an example microplate.

FIG. 2 is a close-up schematic side view of an exemplary RWG biosensor 102, which has a grating 103 and surface 105 configured so that a select biological substance 104 affixes thereto. RWG biosensors 102 need to be supported so that they can be optically interrogated. The typical support structure is called a "microplate." FIG. 3 is a face-on view of an example microplate 170 that comprises a support plate 171 with a surface 173 having a plurality of wells 175 formed therein. An example support plate 171 has a two-part construction of an upper plate 171U and a lower plate 171L, such as shown in the partial view of FIG. 4 and as described for example in U.S. Patent Application Publication No. 2007/0211245.

Microplate 170 of FIG. 3 illustrates an exemplary configuration where RWG biosensors 102 are arranged in an array 102A and operably supported in wells 175. An exemplary RWG biosensor array 102A has a 4.5 mm pitch for RWG biosensors 102 that are 2 mm square, and includes 16 RWG biosensors per column and 24 RWG biosensors in each row. In embodiments, fiducials 179 are used to position, align, or both, the microplate 170 in system 100. A microplate holder 174 is also shown holding microplate 170. Many different types of plate holders can be used as a microplate holder 174.

With reference again to FIG. 1, system 100 includes a tunable light source 106 according to the present disclosure and discussed in greater detail below. Tunable light source 106 is configured to generate a narrow-wavelength light beam 134 having a spectral bandwidth and a predetermined sequence of distinct central wavelengths over a predetermined time period. In embodiments, tunable light source 106 is configured to emit a series of narrow-band light beams 134 having respective central wavelengths ranging from 838 nm to 853 nm at a tuning speed of 0.1 nm/sec to 300 nm/sec.

Although tunable light source 106 is shown emitting light beam 134 into free space, guided-wave configurations that use optical waveguides (e.g., optical fibers) can also be selected.

Light beam 134 from light source 106 passes to imaging system 114 and to illumination optical system 130, which has an associated optical axis A1. Illumination optical system transforms light beam 134 into at least one incident light beam (incident light) 134I. Incident light beam 134I passes through a beam splitter 126 and is incident over an area 135 of microplate 170, wherein area 135 includes one or more RWG biosensors 102 (e.g., 4×3 wells of a 384 well-formal microplate 170, just one RWG biosensor, or over all of the RWG biosensors). In one example, incident light beam 134I is moved (scanned) over the RWG biosensor 102 to cover different areas 135 by either moving scanning illumination optical system 130 or by moving microplate 170 via microplate holder 174.

Incident light beam 134I reflects from the one or more RWG biosensors 102, thereby forming a reflected light beam (i.e., reflected light) 134R. Reflected light beam 134R is directed by beam splitter 126 to optical imager 140, which in an example includes an imaging lens 142 and an image sensor 144 that captures an electronic (i.e., digital) image 145 (see FIG. 5) of the illuminated area 135 that includes the one or more RWG biosensors 102. Image sensor 144 generates a raw electronic image signal 5145 representative of the captured electronic image. Optical imager 140 also includes image-sensor electronics 146 that pre-processes raw electronic image signals S145 from the image sensor and generates a pre-processed electronic image signal S146 representative of the pre-processed digital image. An example image sensor 144 is a charge-coupled device (CCD) chip such as the KAI-0340 CCD chip with a pixel size of 7.4 microns, available from Kodak, Inc., Rochester, N.Y., or a complementary metal oxide semiconductor (CMOS) chip. An example optical imager 140 is a CCD camera such as the Prosilica GE680 GigE camera, available from Prosilica, Burnaby, British Columbia, Canada, which camera has a maximum frame rate of 215 fps at VGA resolution. In embodiments, image sensor 144 can be an array of one or more photodiodes.

System 100 also includes a controller 150 having a processor unit ("processor") 152 and a memory unit ("memory") 154. Example processors 152 include a computer, microprocessor, one or more central-processing units (CPU), a field-programmable gate array (FPGA) or the like. Memory 154 can be any type of digital memory used in computers, such as solid-state memory, magnetic memory, and optical memory. Controller 150 receives pre-processed electronic image signals 5146 from image-sensor electronics 146 and stores them in memory 154. Processor 152 analyzes the digital images 145 embodied in pre-processed electronic signals 5146 based on instructions (e.g., image-processing software) stored therein or in memory 152. This process is discussed in greater detail below.

In embodiments, controller 150 includes or is operably connected to a display unit 156 that displays measurement information such as spectra plots, resonant wavelength plots, and other measurement results, as well as system status and performance parameters. In embodiments, the spectra can be processed directly so that only the resonant wavelengths (as calculated, for example, as the respective centroids of measured spectra) are stored in memory 154.

Example RWG biosensors 102 make use of changes in the refractive index at sensor surface 105 that affect the waveguide coupling properties of incident light beam 134I and reflected light beam 134R to enable label-free detection of biochemical substance 104 (e.g., cell, molecule, protein, drug, chemical compound, nucleic acid, peptide, carbohydrate) on the RWG biosensor. A biochemical substance 104 may be located within a bulk fluid deposited on RWG biosensor surface 103, and the attachment of this biochemical substance to the sensor surface alters the index of refraction at the RWG.

To detect biochemical substance 104, RWG biosensor 102 is probed with incident light beam 134I, and reflected light beam 134R is received at optical imager 140. Optical imager 140 is synchronized with tunable light source 106 so that as the wavelength of incident optical light beam 134I is swept over the wavelength band (to generate a series of optical light beams 134I of different central wavelengths), the optical imager captures a series of digital images 145 corresponding to the different wavelengths. Thus, optical imager obtains a sequence or series of RWG biosensor images 145, each of which corresponds with one of the distinct wavelengths emitted from the tunable light source 106.

Figure 5:
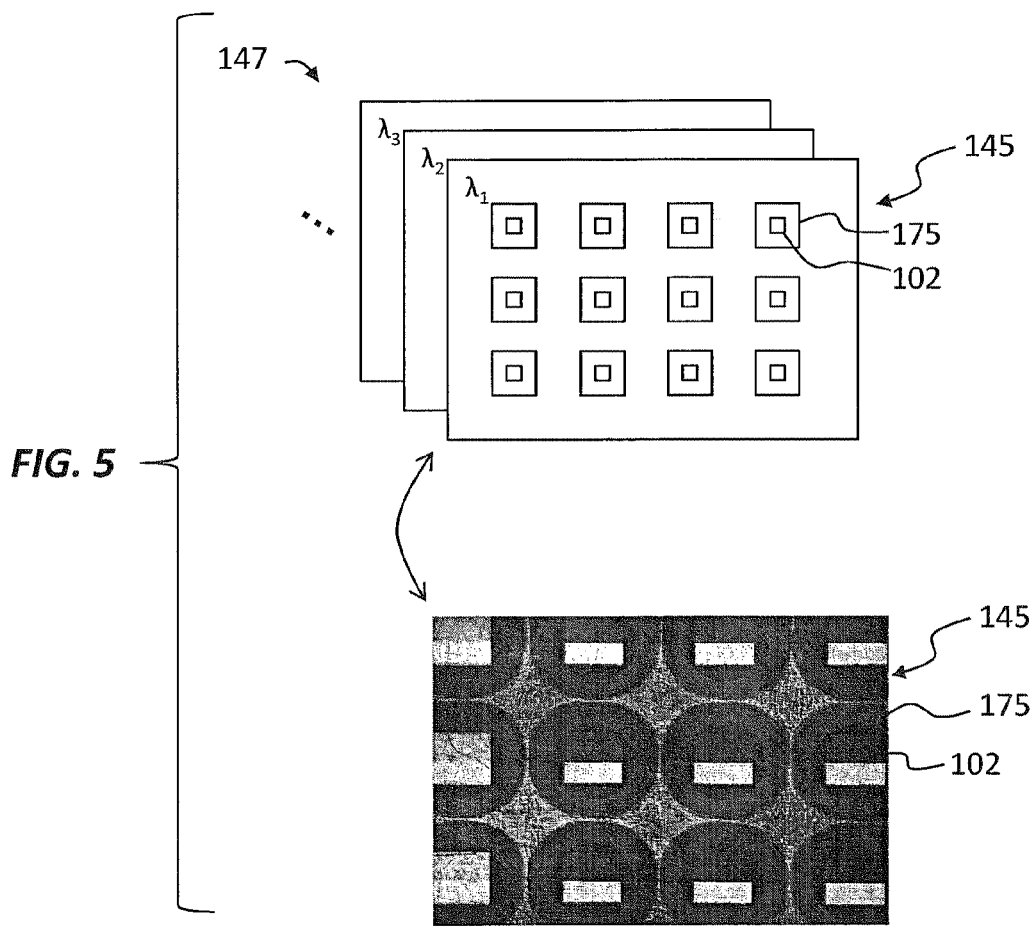
FIG. 5 is a schematic diagram illustrating a collection of digital images associated different wavelengths of incident illumination provided by the tunable light source.

FIG. 5 schematically illustrates this collection 147 of images 145 for different (central) wavelengths $\lambda_1, \lambda_2, \ldots \lambda_j \ldots \lambda_n$, which collection constitutes a "three-dimensional" (3D) data file or "data cube" of images. FIG. 5 also includes an example of an actual image 145. Optical imager 140 takes a sequence or series of images or pictures of the RWG biosensor(s) 102, where each image corresponds with one of the distinct central wavelengths $\lambda_j$ of the series of light beam 134 emitted from tunable light source 106. Lastly, processor 152 receives and processes collected images 147 to determine for example whether or not there was a biochemical interaction or other event on one or more of RWG biosensors 102.

Controller 150 is configured (e.g., processor 152 is programmed or operates under the control of software stored in memory 154) to determine if there are any changes (e.g., 1 part per million) in the RWG biosensor refractive index caused by the presence of biological substance 104. In embodiments, RWG biosensor surface 105 can be coated with, for example, biochemical compounds (not shown), or like biologically or chemically active materials, that only allow surface attachment of specific complementary biochemical substances 104 such as antibodies or proteins, thereby enabling RWG biosensor 102 to be both highly sensitive and highly specific. In this way, system 100 and RWG biosensor 102 can be used to detect a wide variety of biological substances 104. Likewise, RWG biosensor 102 can be used to detect the movements or changes in cells immobilized to RWG biosensor surface 103, for example, when the cells move relative to the RWG biosensor or when they incorporate or eject material, a refractive index change occurs.

If multiple RWG biosensors 102 are operably supported as an array 102A in wells 175 of microplate 170, which in turn is supported by microplate holder 174, then they can be used to enable high-throughput drug or chemical screening studies. For a more detailed discussion about the detection of a biological substance 104 (or a biomolecular binding event) using scanning optical reader systems, see U.S. patent application Ser. No. 11/027,547. Other optical reader systems are described in U.S. Pat. Nos. 7,424,187, 7,599,055, and 7,576,333, and U.S. Patent Application Publications No. 2006/0205058 and 2007/0202543.

Controller 150 and memory 154 therein receive collected pre-processed images 145 via pre-processed electronic image signals 146 for each central wavelength in incident light beam 134I, with the collected images 147 forming the aforementioned "data cube" shown in FIG. 5. Processor 152 then uses image processing software to automatically process the collected images to, for example: 1) determine whether or not there was a biochemical interaction or other event on one or more of the illuminated RWG biosensor(s) 102; 2) locate sensor region(s), reference region(s), or both, on each of the illuminated RWG biosensor(s) 102; 3) remove defect regions on each of the illuminated RWG biosensor(s) 102; 4) calibrate a uniformity of surface chemistry and target molecule immobilizations on each of the illuminated RWG biosensor(s) 102; or a combinations thereof.

If desired, processor 152 can bin together multiple imaging regions (pixels) with prior knowledge about the locations of sensor and reference regions (not shown) on RWG biosensors 102. In this mode, multiple pixels are grouped together as a single detector and the number of sensor spectra/images can be reduced to the number of binned regions. In this way, the data processing can be greatly simplified.

To achieve a data rate of 1 Hz for a specific interrogation application, the sequential scanning of tunable light source 106 and the sequential acquisition of the spectral images 145 captured by optical imager 140 needs to be completed in 1 second. This requirement is well within the current capability of tunable light source 106. Of course, to meet this capability or any other data rate, the number of desired wavelength sampling points dictates the frame rate of image sensor 144 (and associated image-sensor electronics 146). For example, to obtain 500 wavelength samples during a single tuning sequence, the frame rate needs to be as fast as 500 frames per second (fps). An optical imager 140 in the form of a CMOS camera such as the Basler A504k is able to deliver 500 fps at a full 1024×1208 pixel format, with a higher frame rate being possible for partial-area images. In an application where it is not necessary to achieve a 1 Hz data rate, a slower optical imager 140 can be used.

Example Imaging Systems

Figure 6:
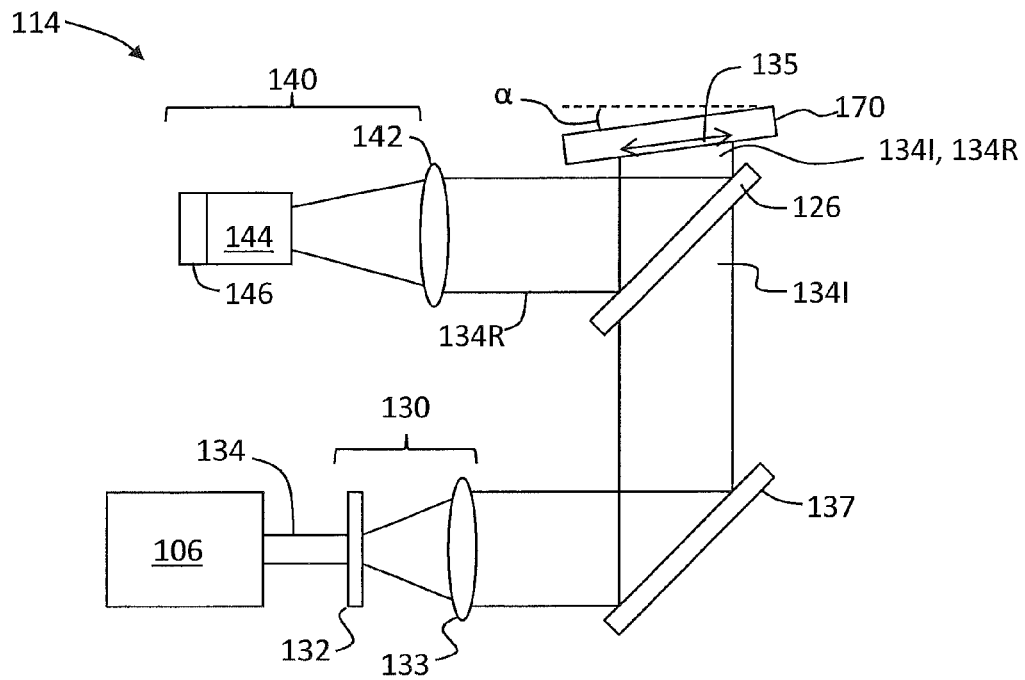
FIG. 6 through FIG. 9 illustrate different embodiments of the optical imager of the optical reader system of FIG. 1.
Figure 7:
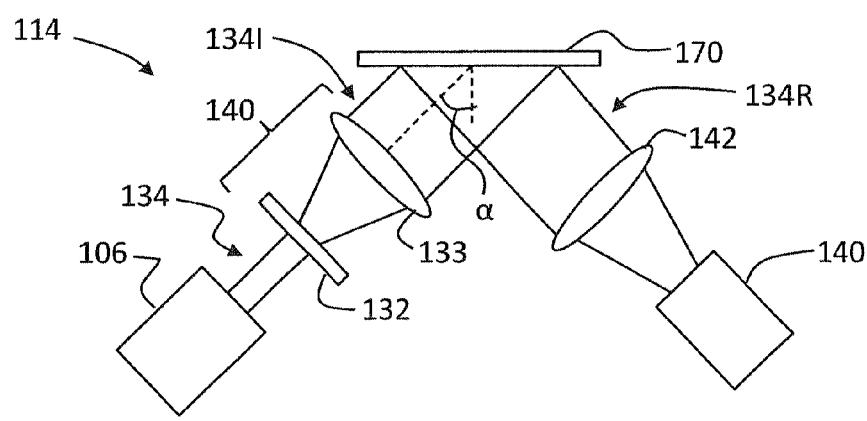
Figure 8:
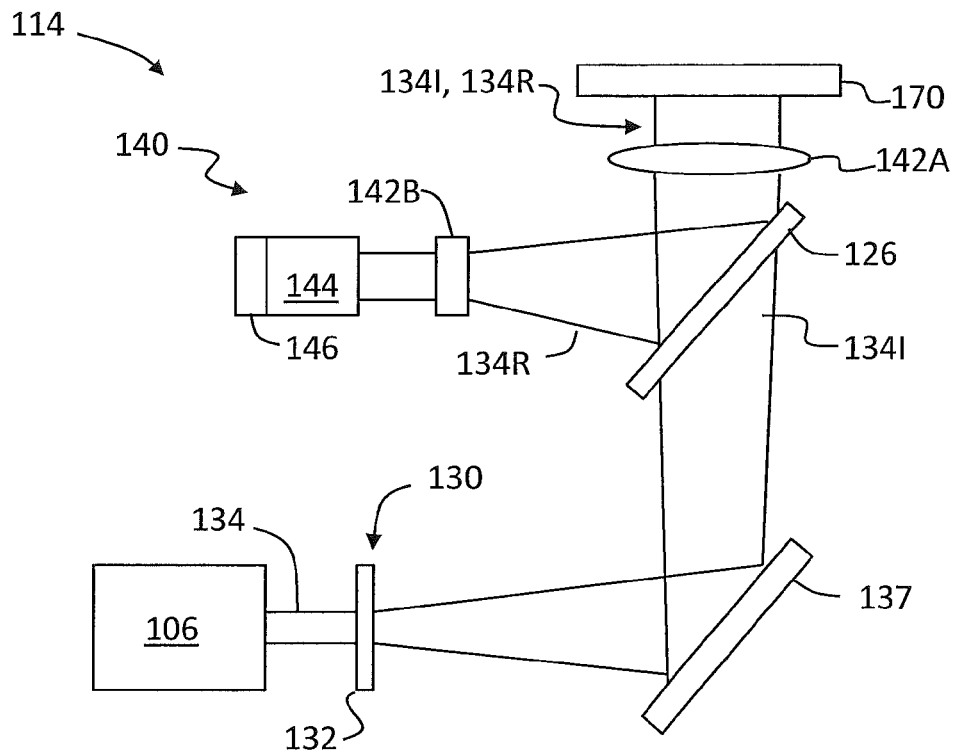

Four exemplary imaging systems 114 and their operation are now discussed with respect to FIG. 6 through FIG. 8. In FIG. 6, the imaging system 114 shown has a normal to near-near normal incident angle α at microplate 170, where the illumination optical system 130 includes a lens 132 that receives the light beam 134 and directs it towards a collimating lens 133. The collimating lens 133 forms from light beam 134 a collimated interrogation beam 134I and directs it towards a fold mirror 137. Fold mirror 137 reflects the collimated interrogation beam 134I to travel through beam splitter 126 and illuminate a predetermined number of RWG biosensors 102 located within the wells 174 of microplate 170 over area 135. Alternatively, the illumination optical system 130 is configured to form multiple interrogation beams 134I, where each interrogation beam illuminates a corresponding RWG biosensor 102 located within a well 175 of microplate 170. In addition, the optical imager 140 has a telecentric imaging lens 142 with a field of view selected to collect an image 145 from the illuminated RWG biosensor(s) 102.

FIG. 7 is a schematic diagram of an example imaging system 114 wherein incident light beam 134I has an oblique (i.e., non-normal) incidence angle α. The non-normal incidence angle α eliminates the need for beam splitter 126 and can improve the optical efficiency by a factor of four. In this embodiment, illumination optical system 130 includes a lens 132 that receives light beam 134 and directs it at a predetermined angle towards a collimating lens 133. The collimating lens 133 receives light beam 134 and outputs a collimated interrogation beam 134I that it illuminates a predetermined number of RWG biosensors 102 located within the wells 175 of the microplate 170. Alternatively, the illumination optics 130 can be configured to form multiple interrogation beams 134I, where each interrogation beam illuminates a corresponding RWG biosensor 102. In addition, optical imager 140 has a telecentric lens 142 positioned at a predetermined angle and having a field of view selected to collect an image 145 from the illuminated RWG biosensor(s) 102.

Referring to FIG. 8, there is shown an exemplary imaging system 114 having a relatively small footprint because the illumination optics 130 and the imaging optics 140 share a front lens (or lens group) 142A of the telecentric lens 142. In this embodiment, lens 132 of illumination optical system 130 receives light beam 134 and directs it in a diverging manner to fold mirror 137. Fold mirror 137 reflects divergent light beam 134 to travel through beam splitter 126 and to front lens 142A. Front lens 139 forms interrogation beam 134I that illuminates a predetermined number of biosensors 102 located within the wells 175 of the microplate 170. Front lens 142A also collects reflected light 134R and directs it to beam splitter 126. Beam splitter 126 directs reflected light 134R toward lens 142B, which images reflected light 134R onto image sensor 144 as discussed above.

Figure 9:
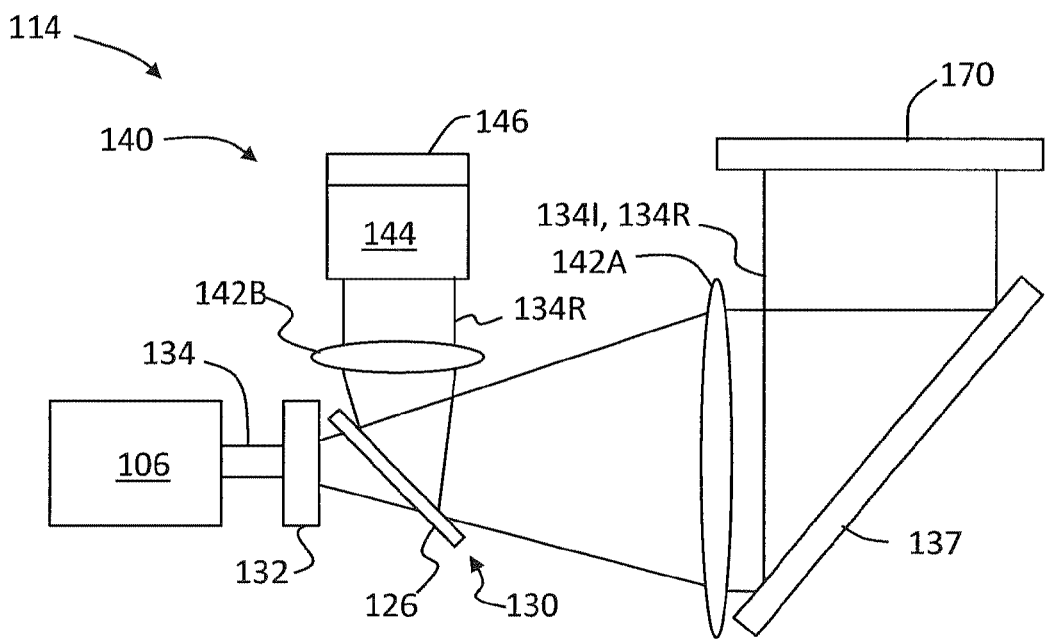

FIG. 9 is a schematic diagram of an example imaging system 114 where the illumination optics 130 and the imaging optics 140 share a front lens 142A of the telecentric lens 142. Lens 132 of illumination optical system 130 receives the light beam 134 and directs it through beam splitter 126 towards front lens 142A via fold mirror 137. Front lens 142A collimates light beam 134 and forms interrogation beam 134I. Front lens 142A also collects reflected light 134R from microplate 170 and RWG biosensors 102 therein and directs it back to beam splitter 126 via fold mirror 137. Beam splitter 126 then directs reflected light 134R to the second lens 142B of optical imager 142 and images reflected light 134R onto image sensor 144 as discussed above.

Tunable Light Source

Figure 10:
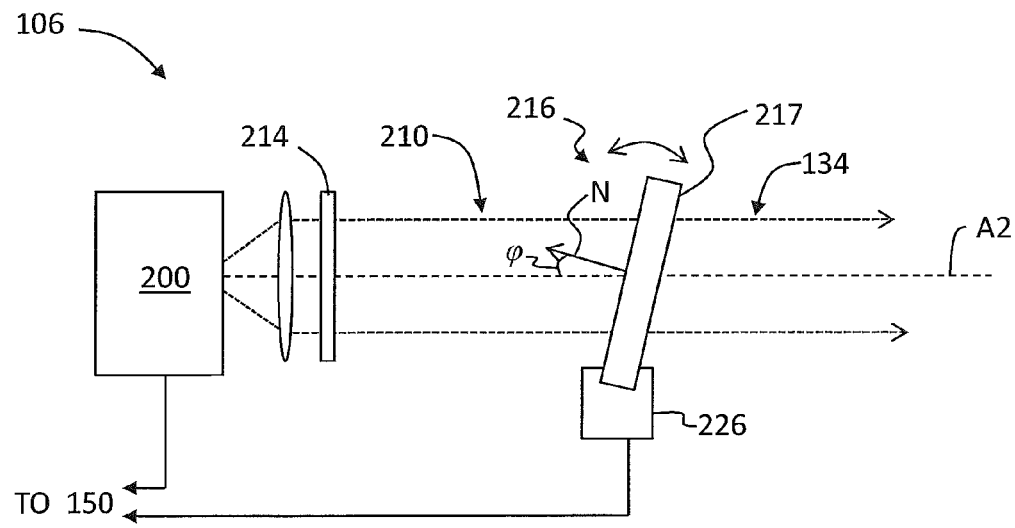
FIG. 10 is a schematic diagram illustrating an example embodiment of a single-pass tunable light source for use in the optical reader system of FIG. 1.

FIG. 10 is a schematic diagram of an example tunable light source 106 that includes a broadband light source 200, such as a superluminescent diode (SLD), as available from Superlum Diodes, Ltd., Moscow, Russia. An example SLD light source 200 has a spectral bandwidth W of 20 nm and center wavelength of about 840 nm. One or more conventional broadband LEDs can also be used as broadband source 200 provided that the light is sufficiently collimated. Examples of an LED-based source 200 are discussed in greater detail below. Broadband light source 200 emits a broadband light beam 210 along a light source axis A2. In embodiments, broadband light source 200 has a spectral bandwidth W in the range from 10 nm to 40 nm.

Tunable light source 106 also includes a tunable wavelength filter ("tunable filter") 216 arranged along axis A2. Example tunable filters 216 include a filter member 217 and a filter support 226. Example tunable filters include a monochromator with an adjustable (e.g., motorized) diffraction grating, a tunable Fabry-Perot etalon that employs actuators (e.g., piezoelectric or MEMS actuators), a liquid crystal tunable filter, an acousto-optic tunable filter, and an angle-adjustable Fabry-Perot etalon. Of these example tunable filters, the angle-adjustable filter provides a good balance of performance and cost. This type of tunable filter 216 is discussed below in connection with tunable light source 106.

Tunable filter 216 is configured to transmit light over a spectral linewidth having a center wavelength, and its "tunability" refers to its ability to adjust the central wavelength while maintaining the spectral linewidth substantially constant. Thus, the transmission function of tunable filter 216 essentially shifts along with the central wavelength.

In an example, tunable light source 106 includes a polarizer 214 arranged along optical axis A2 between broadband light source 200 and tunable filter 216 to linearly polarize broadband light beam 210 to have P-polarization or S-polarization.

In some cases, an S-polarization configuration for polarizer 214 is used because it accommodates wider incident beam angles than a P-polarization configuration.

Filter member 217 makes an angle φ relative to axis A2 (along which incident broadband light beam 210 travels) and is measured relative to the surface normal N of the tunable filter. In an example embodiment, broadband light beam 210 is collimated using a collimating lens 202. Tunable filter 216 is configured so that broadband light beam 210 is converted to narrower-band (filtered) light beam 134 when the broadband light beam passes through filter member 217. In an example, filter member 217 is supported by filter support device 226 that in one example is adapted to adjust the orientation of (i.e., angle φ) of filter member 217 relative to optical axis A2 to adjust the wavelength of the narrow-band collimated light beam 134. Example tunable filters 216 are discussed in greater detail below.

Figure 11:
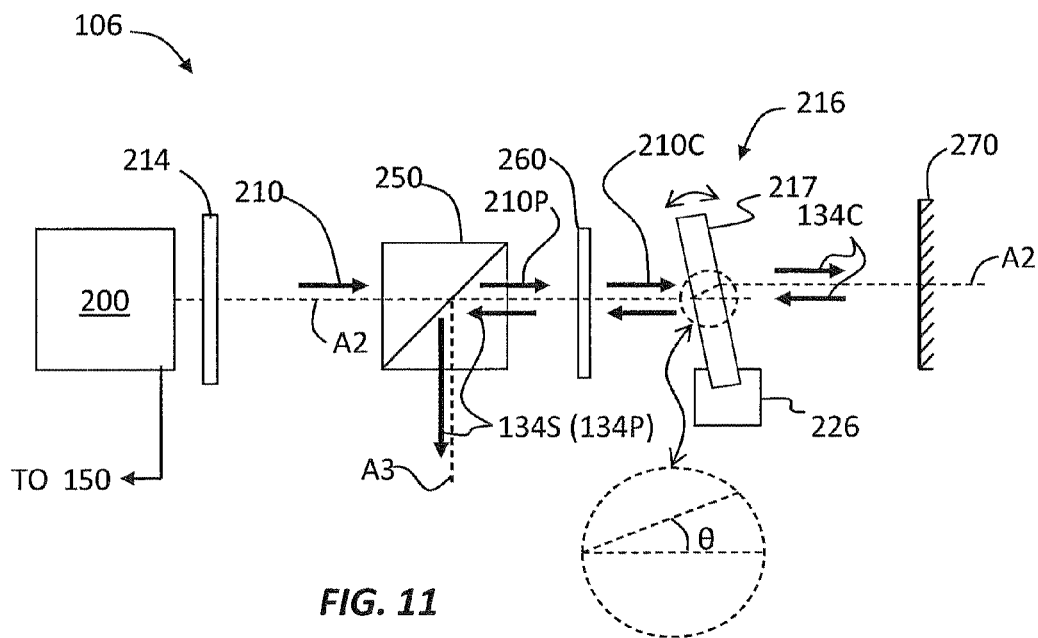
FIG. 11 is a schematic diagram illustrating an example embodiment of a double-pass tunable light source for use in the optical reader system of FIG. 1.

FIG. 11 is a schematic diagram of another embodiment of tunable light source 106 similar to that of FIG. 10 and that further includes along optical axis A2 a polarizing beam splitter 250 and a quarter-wave plate 260 between broadband light source 200 and tunable filter 216. A fold mirror 270 is arranged along optical axis A2 adjacent tunable filter 206 but on the side opposite quarter-wave plate 260 (i.e., the tunable filter resides between the quarter-wave plate and the fold mirror).

In the tunable light source 106 of FIG. 11, collimated broadband light beam 210 is P-polarized by passing through P-polarizer 214, which forms P-polarized light beam 210P. This beam passes directly through polarizing beam splitter 250 and to quarter-wave plate 260, which converts the polarization of P-polarized broadband light beam 210P to form a circularly polarized broadband light beam 210C. This circularly polarized light beam then travels through filter member 217, thereby forming a narrow-band light beam 134C that is also circularly polarized. This narrow-band light beam reflects off of fold mirror 270 and stays circularly polarized. Narrow-band light beam 134C travels back through filter member 217, which has already band-narrowed this beam, and then passes through quarter-wave plate 260, which converts the polarization to form an S-polarized narrow-band light beam 134S. This light beam is reflected by polarizing beam splitter 250 along an axis A3, which is at right angles to optical axis A2.

Note that the offset of axis A2 that occurs upon passing through filter member 217 is compensated by the two-way optical path through the filter member. Tunable light source 106 can be configured so that the polarization of broadband light beam 210 can start out S-polarized and form an output P-polarized narrow-band light beam 134P, as long as the RWG biosensor(s) 102 being interrogated are oriented for transverse magnetic (TM) interrogation, and as long as polarizing beam splitter 250 is properly configured.

As discussed above, broadband light source 200 has a spectral bandwidth W sufficient to cover the dynamic range and wavelength variation of the RWG sensors 102 to be interrogated. An example minimum spectral bandwidth is W=10 mm. The spectral linewidth (i.e., bandpass) of tunable filter 216 is preferably selected for optimum RWG sensor interrogation performance. A wide filter spectral linewidth increases the total optical power, but broadens the measured sensor spectrum, thereby reducing the detection sensitivity.

In general, the interrogated spectrum (i.e., the spectral linewidth of reflected light 134R) is the convolution of the "filter function" (i.e., the spectral linewidth of tunable filter 216) and the RWG sensor resonance function. For simplicity, a Gaussian profile is assumed for both functions, with filter and biosensor spectral linewidths of $w_f$ and $w_g$, respectively. The measured spectrum S is given by:

$$S = \int d\lambda' \exp\left(-\frac{\lambda'^2}{w_g^2}\right) \exp\left(-\frac{(\lambda' - \lambda)^2}{w_f^2}\right) \quad (1)$$

The resulting function is also Gaussian with a width of $\sqrt{w_f^2 + w_g^2}$ and an amplitude that is proportional to $$\frac{w_f w_g}{\sqrt{w_f^2 + w_g^2}}.$$

Since the detection sensitivity of the wavelength centroid (i.e., resonant wavelength $\lambda_R$) is proportional to the square root of the amplitude and inversely proportional to the square root of the width, a detection merit function M can be expressed as:

$$M = \frac{w_f w_g}{w_f^2 + w_g^2} \quad (2)$$

The condition that maximizes this merit function is $$w_f = w_g. \quad (3)$$

The optimum filter spectral linewidth is therefore the same as that for the spectral linewidth of the RWG biosensor resonance ("biosensor resonance linewidth"). An example full width at half maximum (FWHM) of the RWG biosensor resonance linewidth is $w_g$=0.8 nm, which is relatively small when compared to the light source spectral bandwidth W of between 10 nm and 40 nm.

In reality, both the filter spectral linewidth and the biosensor resonance linewidth may differ from a Gaussian profile. However, the condition of equation (3) provides useful guidance since both functions are bell-shaped and their difference from a Gaussian is small. Note that since the biosensor resonance linewidth and the filter spectral linewidth have a non-zero spectral width, the "wavelength" of filtered light beam 134 refers to its central wavelength.

In embodiments, the FSR of tunable filter 216 can be designed to be at least as wide as the spectral bandwidth W of broadband light source 200. Since the tuning wavelength range requirement for biosensor interrogation is only about 10 nm, the filter spectral linewidth shape is nearly constant within the small range of incident angles φ. A single-cavity filter may be preferred over more complicated multiple cavity designs in applications requiring better yield. In cases where a large range of incident angles φ is required for wavelength tuning, it may be best to use S-polarized light, which has less angular sensitivity. An example narrow range of incident angles is φ between 0° and 6°, while an example broader range of incident angles is φ between 0° and 14°.

Design of the Broadband Light Source

If the total output power of broadband source 200 is P and the spectral bandwidth is W, the peak total output power p in light beam 134 after passing through tunable filter 216 is given by $$p = \frac{w_f W}{\sqrt{w_f^2 + W}} P \approx \frac{w_f}{W} P \qquad (4)$$

The above approximation assumes W>>$w_f$. The peak power upon reflection from RWG sensor 102 is $$\frac{w_f}{\sqrt{2W}} P,$$

which is the equivalent power level of a narrow band tunable laser. SLD broadband light sources 200 having a 20 nm FWHM at power levels of 20 mW and 100 mW are commercially available. The equivalent power level for RWG biosensors 102 with a 0.8 nm biosensor resonance linewidth is 0.56 mW and 2.8 mW, respectively. These power levels are sufficient for swept wavelength detection.

Angle-Tuned Filter

The spectral transmission of a Fabry-Perot etalon can be expressed as:

$$I = \frac{I_0}{1 + (2F/\pi)^2 \sin^2\left(\frac{\pi\lambda}{FSR}\right)} \qquad (5)$$

where the finesse is given by $$F = \frac{\pi\sqrt{R}}{1-R} \qquad (6)$$

and the free spectral range FSR is given by $$FSR = \frac{\lambda_0^2}{\Delta} \qquad (7)$$

where $\Delta$ is the optical path length difference, which can be expressed as:

$$\Delta = 2nd \cos\theta. \qquad (8)$$

Here, $\theta$ is the internal incident angle in the cavity (see inset, FIG. 11), n the index of refraction, and d the thickness of the cavity. The FWHM of the filter spectral linewidth is simply FSR/F.

Figure 12:
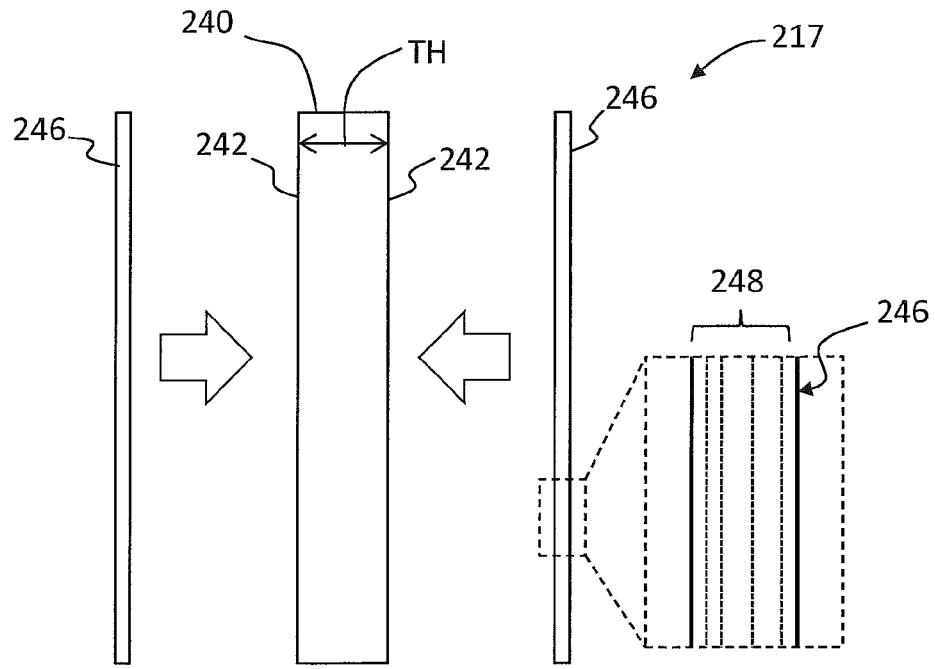
FIG. 12 is a schematic exploded side view of an example filter made from a thin glass substrate and optical coatings formed from thin films.

FIG. 12 is a schematic exploded side view of an example filter member 217 made from a thin glass substrate 240 with opposing sides 242. Thin glass sheets used for flexible displays can be used as glass substrate 240. To maintain mechanical rigidity, in an example the thickness TH of substrate 240 is preferably greater than 25 microns, which translates to a FSR of 9.3 nm Reflective coatings 246 are preferably deposited on one or both sides 242, with the reflectivity designed to produce the desired filter spectral linewidth over a given angular range. Reflective coatings 246 typically include one or more thin-film layers 248.

Figure 13:
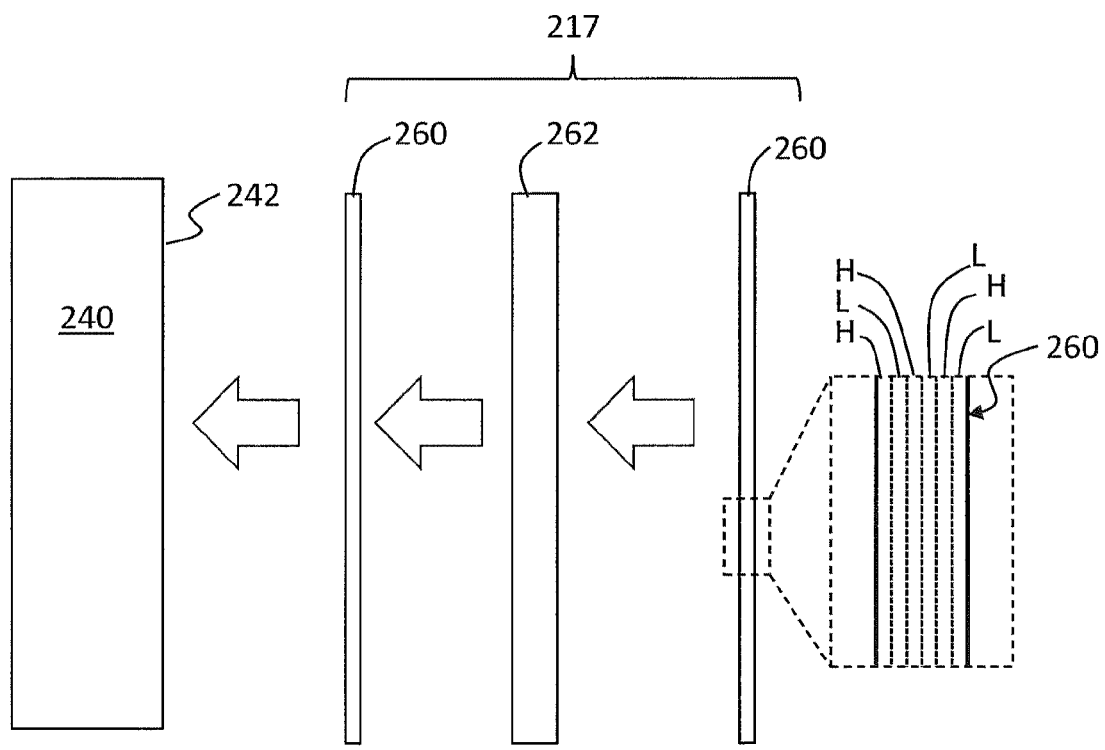
FIG. 13 is a schematic exploded side view of an example filter made by depositing material to form two reflective layers sandwiching a cavity layer, with the deposited layers mechanically supported by a glass substrate.

FIG. 13 is a schematic exploded side view similar to FIG. 12 that illustrates another example filter member 216, where a relatively thick glass substrate 240 is used to mechanically support a thin-film stack of deposited material that serves as the tunable filter. Two reflective layers 260 sandwich a solid cavity layer 262, thereby forming a single-cavity filter member 217. Multiple-cavity filters with a square band pass similar to that of dense wavelength division multiplexing (DWDM) filters can be fabricated using like layers. The thin-film-stack filter member 217 of FIG. 13 has the advantage that the deposition process allows for good control of the thickness and uniformity of layers 260 and 262 and therefore better control over the filter spectral linewidth.

In an exemplary embodiment where filter member 217 of FIG. 13 is used for the double-pass tunable light source design of FIG. 11, reflective layers 260 comprise a stack of high-reflectivity H and low-reflectivity L coatings (films) in an HL-HL-HL (i.e., (HL)$^3$) configuration, while cavity layer 262 comprises a layer of $SiO_2$, which in an example embodiment is 12 microns thick. In embodiments, $MgF_2$ can be used for low index quarter-wave coating L, and $TiO_2$ for high index quarter-wave coating H. An example filter member 217 has a thickness of about 2 mm and can be diced to 10×10 mm$^2$. In embodiments, the center wavelength of filter member 217 can be uniform to within +/−0.1 nm over the filter member area.

Figure 14:
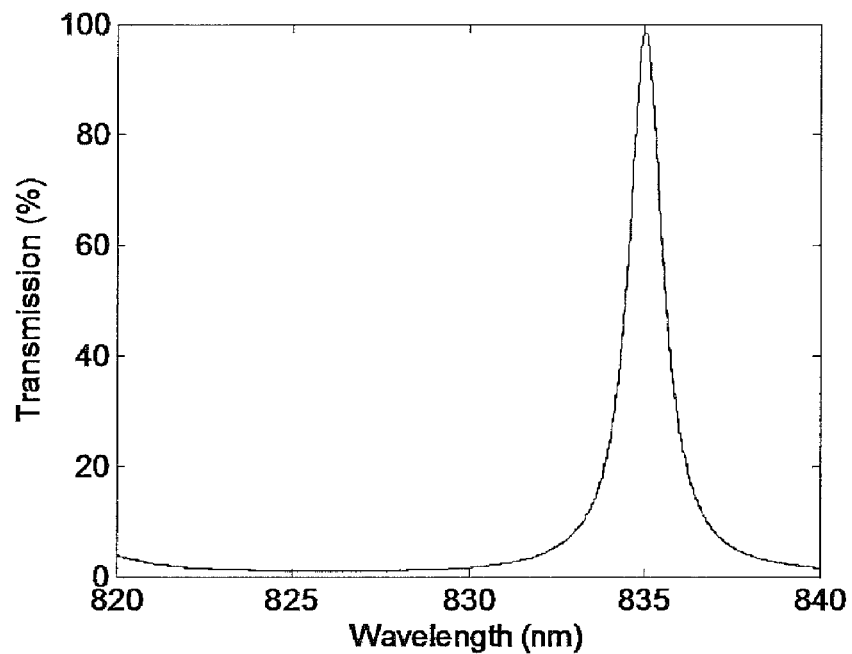
FIG. 14 and FIG. 15 plot the filter spectral linewidth (filter function) as intensity vs. wavelength for an example single-pass filter for incident angles of θ=5° and θ=14°, respectively.
Figure 15:
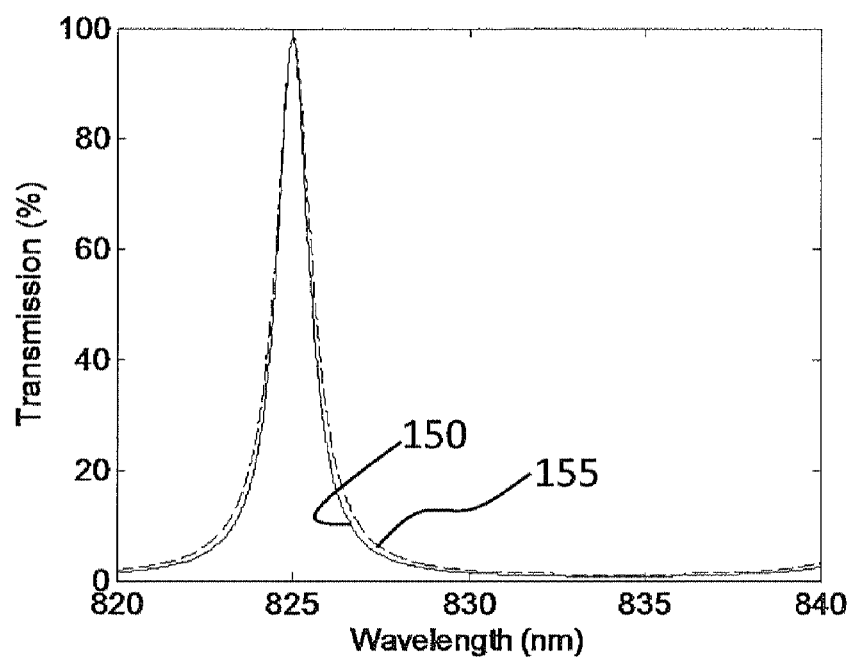

The single-pass filter spectral linewidth (i.e., transmission) for an example tunable filter 216 is plotted for intensity vs. wavelength in FIG. 14 and FIG. 15 for respective incident angles of $\phi=5°$ and $\phi=14°$. A tuning range of 10 nm was achieved while the shape of the filter spectral linewidth remained substantially constant (i.e., the only substantial change in the filter spectral linewidth was a change in the central wavelength). At q=5°, the P-polarization and S-polarization curves essentially overlap as shown by the single trace. At $\phi=14°$, the P-polarization curve is slightly broadened due to the reduction of mirror reflectivity for this polarization. Although angle tuning in not linear, as indicated by the slight differences in the S-polarization curve 150 and P-polarization curve 155 in the transmission plot of FIG. 15, varying the speed of the angle scan can compensate for the nonlinearity and produce a constant-wavelength sweep rate.

For applications where the beam translation needs to be compensated, the double-pass embodiment of tunable light source 106 of FIG. 11 provides such compensation for all tuning angles $\phi$. In embodiments, light beam 210 enters the polarizing beam splitter 250 with the polarization aligned for full transmission by virtue of linear polarizer 214. At small angles $\phi$, the filter spectral linewidth is polarization independent. Because light passes twice through filter member 217, the design width of the single-pass filter spectral linewidth (filter function) is increased by a factor of $\sqrt{2}$.

Figure 16:
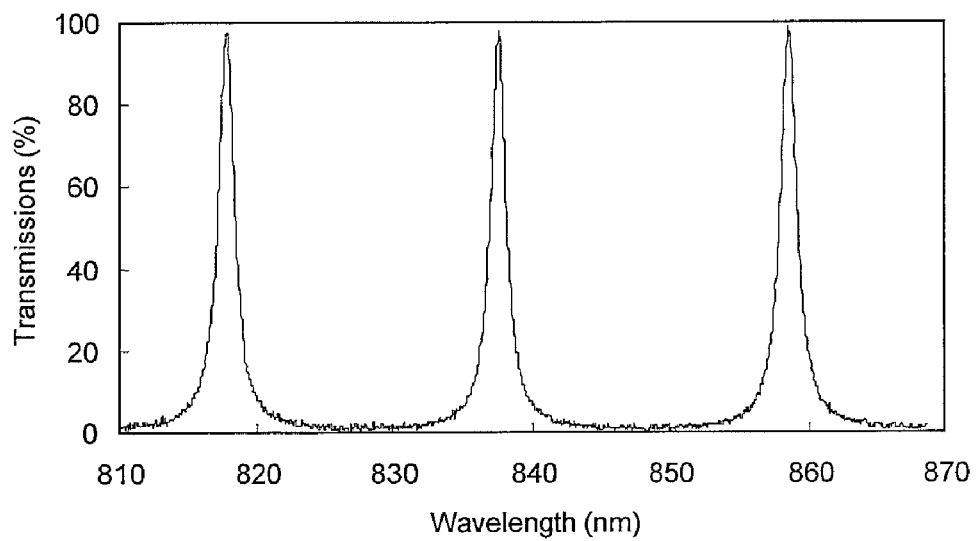
FIG. 16 plots the filter spectral linewidth (intensity vs. wavelength) over a relatively large wavelength range for an example custom filter, and shows that the free spectral range (FSR) is about 20 nm and the targeted normal incidence transmission peak is 838 nm, which is close to the center wavelength of a superluminescent diode (SLD) light source.

FIG. 16 plots the filter spectral linewidth over a relatively large wavelength range for an example custom tunable filter 216, and shows that the FSR 160 is about 20 nm and the targeted normal incidence transmission peak is 838 nm, which is very close to an SLD center wavelength of 840 nm.

As discussed above in connection with FIG. 11, filter member 217 is supported by filter support device 226, which in embodiments can be adapted to adjust the orientation (i.e., incident angle $\phi$) of filter member 217 relative to optical axis A2 to adjust the central wavelength of narrow-band collimated light beam 134 (FIG. 1). Example filter support devices 226 include a rotation stage or a galvanometer scanner. Galvanometer scanners are widely used in industrial applications and are highly reliable and cost effective. Commercially available galvanometer scanners have an angular repeatability of 2 microrad to 8 microrad, which corresponds to a wavelength repeatability of 0.51 pm to 0.13 pm. This error adds about 51 fm to about 13 fm noise to the sensor interrogation error, which is negligible. A filter support device 226 based on a closed-loop galvanometer scanner can operate at a frequency of up to 2 kHz and has a mechanical angle scan range of 12° for a control voltage of ±5 V and a small step response time of 200 microseconds. The center wavelength of the filter spectral linewidth as calibrated as a function of the control voltage for a galvanometer-based filter support device 226 that supports filter 216 is depicted in FIG. 17.

In embodiments, the angular movement of filter support device 226 is controlled by a 16-bit buffered analog voltage waveform generated by a data acquisition board (not shown) in controller 150. The voltage waveform produces a linear wavelength sweep that in one example takes about 2 seconds and covers a wavelength range from 826 nm to 836 nm. Optical imager 140 can be synchronized with the start of the analog voltage output waveform. In embodiments, a total of 400 electronic images 145 are acquired as tunable filter 216 linearly sweeps through the tuning range.

Figure 17:
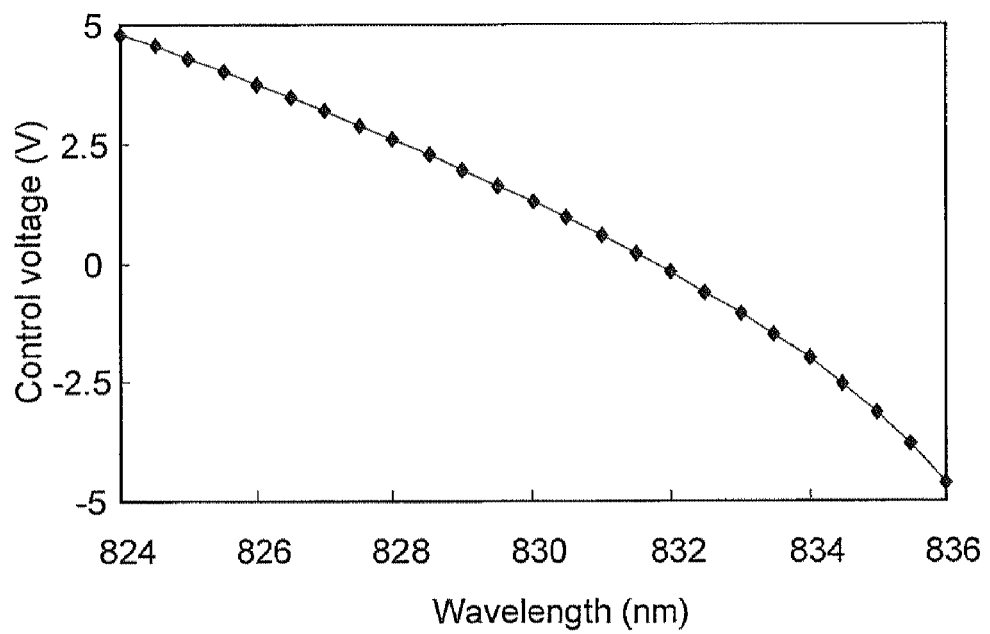
FIG. 17 is a plot of the control voltage (V) vs. central wavelength (nm) for a galvanometer-based filter support device that moveably supports an angle-tuned filter.
Figure 18A:
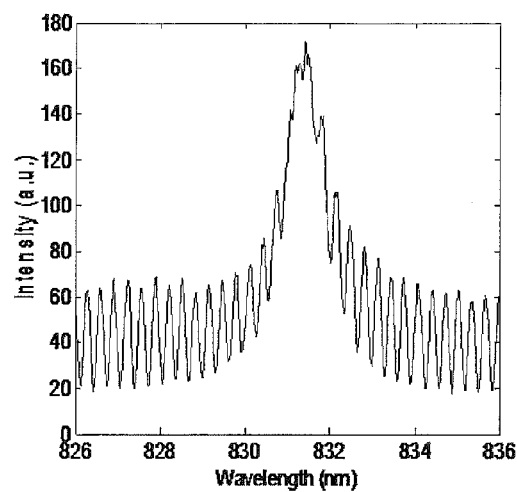
FIG. 18A and FIG. 18B are plots of intensity vs. wavelength showing the interrogated spectra for a single pixel for a tunable laser light source (FIG. 18A) and the tunable light source of the present disclosure (FIG. 18B)

The digital voltage ramp function for a galvanometer-based filter support device 226 is designed based on a calibration curve such as that shown in FIG. 17 to generate a linear wavelength sweep. Digital filtering of electronic images (i.e., sensor spectra) 145 is not necessary because of the convolution of Eq. (1). To illustrate the beneficial effects of a low-temporal-coherence tunable light source 106, the measured interrogated spectra (intensity vs. wavelength) from a single pixel of image sensor 144 was obtained from measuring a series of reflected light beams 135R from RWG biosensor 102 based on a high-temporal-coherence tunable laser light source and the low-temporal-coherence tunable light source 106 of the present disclosure. The respective results are plotted in FIG. 18A and FIG. 18B. Notice the absence of interference fringes in the plot of FIG. 18B, which simplifies the image processing, e.g., no digital filtering is needed to remove parasitic interference fringes in digital image 145. Also, the update rate of system 100 is a relatively quick 3 seconds for a dual-core processor 152. The lack of interference fringes is due to the width of the filter spectral linewidth. Without spectral and spatial parasitic fringes, image sensor 144 can operate in intensity mode, which provides a very high update rate, e.g., up to 200 Hz.

Figure 18B:
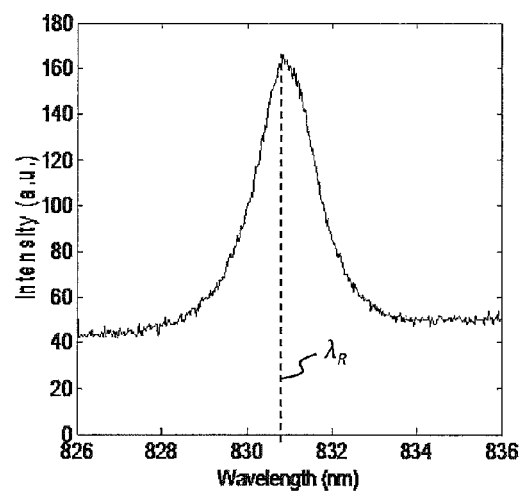

The plot of FIG. 18B represents the convolution of equation (1). In embodiments, the resonant wavelength $\lambda_R$ (shown in the plot as the dashed line) is determined from the data of FIG. 18B by processor 152 applying a centroid algorithm (e.g., $1^{St}$ moment centroid algorithm).

Figure 19:
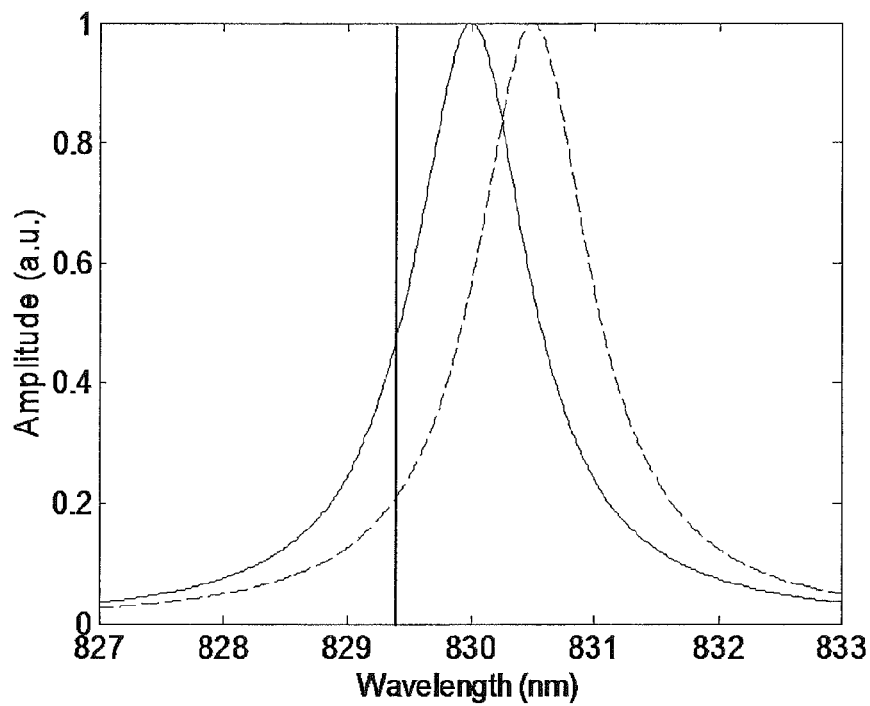
FIG. 19 plots two example biosensor resonance linewidths, and shows the filter central wavelength being fixed to a 50% transmission point of the solid-line biosensor resonance linewidth.
Figure 20:
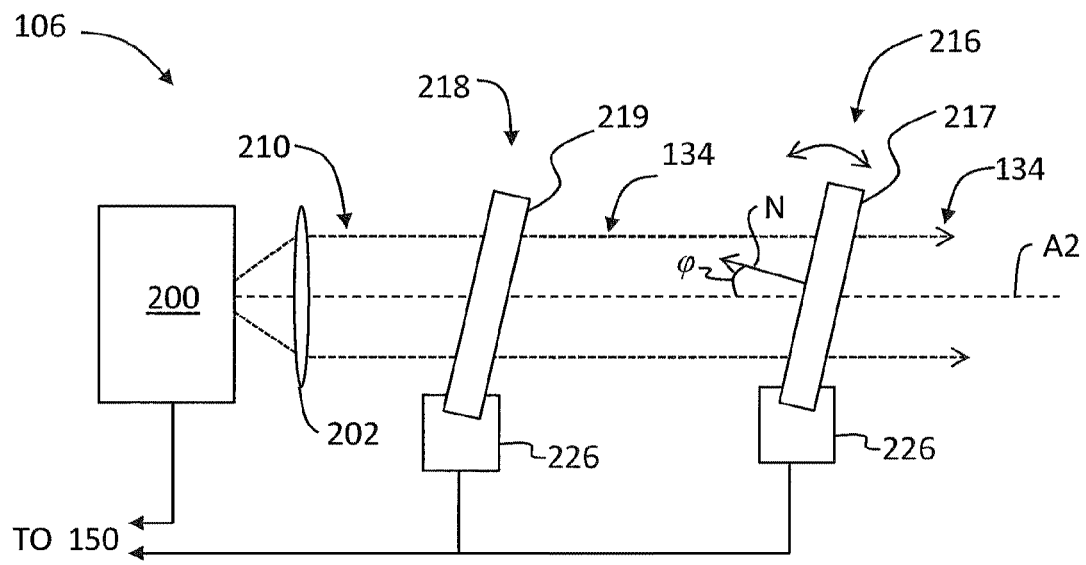
FIG. 20 is similar to FIG. 10 and illustrates an example embodiment of the tunable light source that includes an angularly tunable spectral flatting filter.

FIG. 19 plots two example biosensor resonance spectra and shows the filter central wavelength being fixed to a 50% transmission point of the solid-line biosensor resonance linewidth. A shift of the RWG biosensor resonance wavelength (dashed line curve) is detected as the change in sensor reflectivity and a change in detected intensity at image sensor 144. In this mode, the speed of label-free imaging can be as fast as the frame rate of image sensor 144 and image sensor electronics 146 will allow. This operating mode is suitable for assays having a small dynamic range.

The relationship between detected image intensity and resonant wavelength is calibrated over a useful dynamic range of −0.6 nm to 1.5 nm or −1.5 nm to 0.6 nm, depending on the choice of operating point. This range is sufficient for most cell-based assays. Because of the relatively narrow dynamic range, this technique is suitable for imaging a single or small number of RWG biosensors, where the resonance uniformity and the assay wavelength shifts are within the dynamic range. A wider dynamic range can be achieved by designing a wider biosensor resonance linewidth or filter spectral linewidth. In embodiments, manual wavelength tuning can replace automated (e.g., galvanometer-based) tuning, and the image intensities can be directly converted to digital images 145. This enables a label-free imaging speed to match that of the CCD or CMOS camera, which can be as high as 1 kHz. Such a simple and high speed optical reader is enabled by tunable light source 106.

In an example, controller 150 includes a software interface and displays on display 156 at least one of real-time updated label-free images, differences of label-free images compared to the initial image, and the kinetics of averaged resonance wavelengths in each well. The sequence of label-free images 145 in an assay is saved in a binary file in memory 154 for further data processing.

Spectral Flattening Filter

Figure 21:
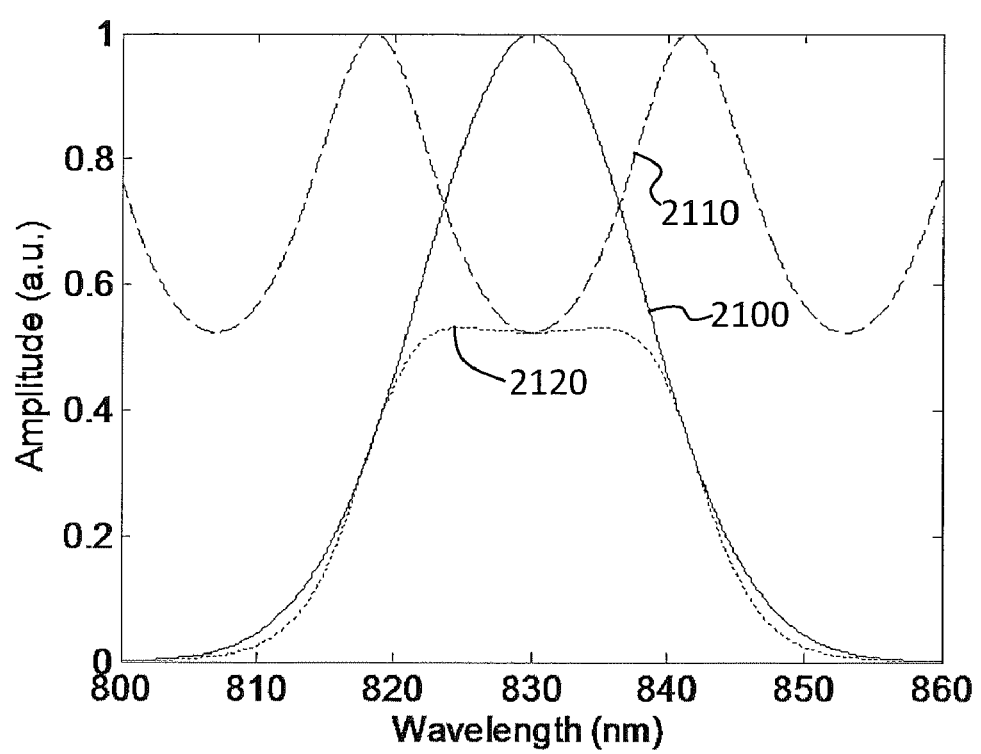
FIG. 21 plots examples of a source spectrum, a filter function (filter spectral linewidth), and a filtered source spectrum (amplitude vs. wavelength)

Broadband light sources 200 such as SLDs and LEDs have a bell-shaped spectra that can be approximated by a Gaussian function. In applications that require constant power over the tuning range, the spectral profile of the broadband source must be flattened. With reference to FIG. 21, in embodiments similar to that shown in FIG. 10, this is accomplished using a spectral flattening filter 218 having a filter member 217 and a filter support device 226, wherein for example filter member 217 comprises an angle-tuned solid etalon. For example, if the broadband source has a FWHM spectral bandwidth of 20 nm, an etalon-based spectral flattening filter 218 can be designed with a finesse of 1.5 and a FSR of 23 nm. The center wavelength of the etalon-based spectral flattening filter 218 is optimized by angle tuning. Examples of source spectrum 2100, a filter function 2110 (filter spectral linewidth), and the flattened source spectrum 2120 are compared in the plot of amplitude vs. wavelength of FIG. 21.

Tunable Light Source with Low Spatial Coherence

As discussed above, example high-brightness broadband light sources include SLDs and nonlinear optical fibers. Such light sources, although temporally incoherent, have substantial spatial coherence. As a result, scattering waves generated from any defects along the optical path interfere coherently with the main wave front, causing interference fringes or speckle patterns even when the temporal coherent length is shorter that the thickness of the RWG sensor substrate.

Figure 22:
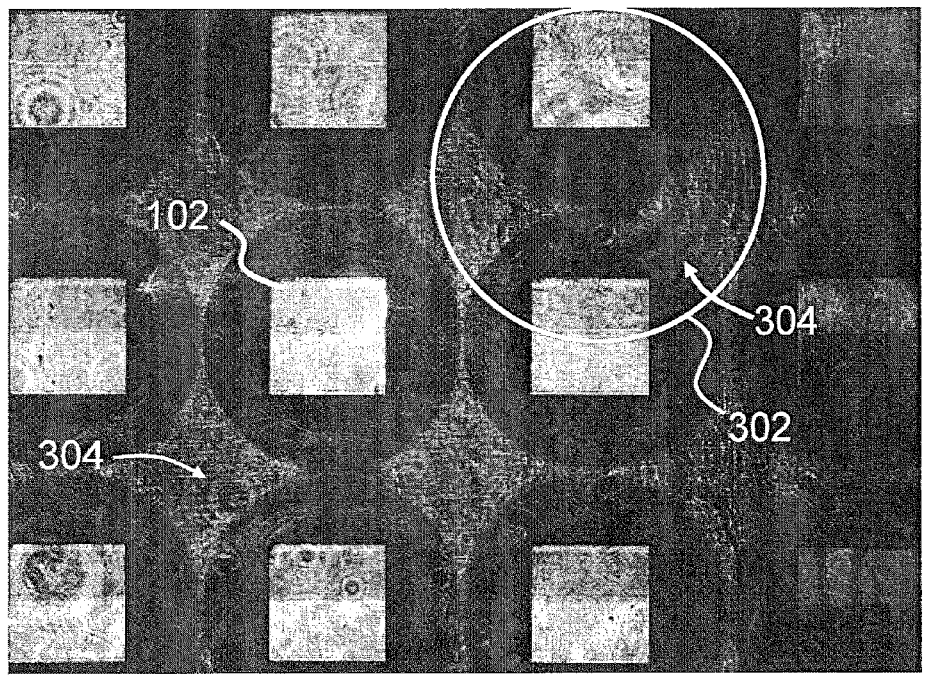
FIG. 22 is a digital image of RWG biosensors illuminated by incident light from a tunable light source that uses a SLD for the broadband light source, with the image showing multiple speckle patterns as a result of the coherence of the incident light.

FIG. 22 is a digital image of RWG biosensors 102 illuminated by incident light 134I from a tunable light source 106 that uses an SLD for broadband light source 200. The white circle 302 encloses an example speckle pattern 304, and there are multiple other speckle patterns 304 in the image.

Speckle patterns 304 adversely affect the performance of an optical reader system by imposing a slowly varying spectral profile that modulates the interrogated RWG sensor response. Furthermore, the interferometric nature of a speckle pattern makes the pattern highly sensitive to temperature and drift, causing artificial shifts in the sensors readouts. These effects adversely impact the accuracy of an optical reader system.

Figure 23:
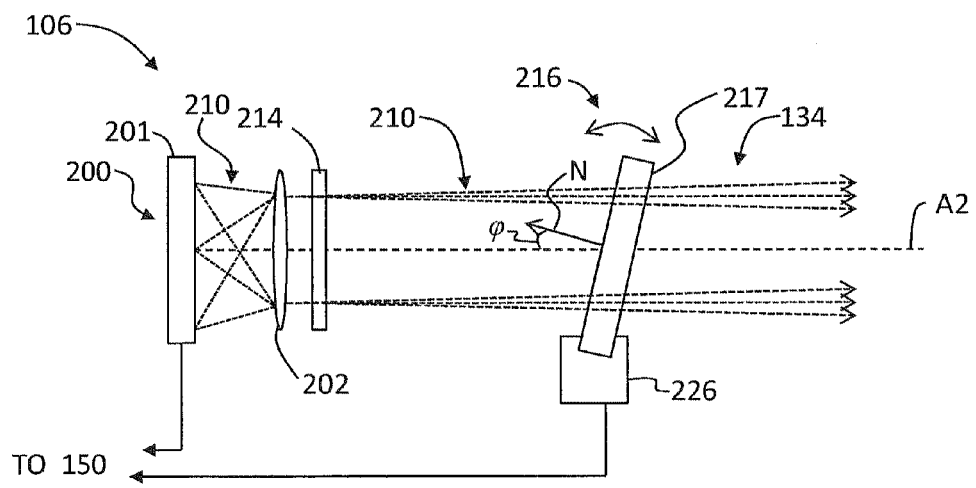
FIG. 23 is a schematic diagram of an example tunable light source similar to FIG. 10, except that the broadband light source comprises an extended-area broadband source that is substantially spatially incoherent.

FIG. 23 is a schematic diagram of an example tunable light source similar to FIG. 10, except that broadband light source 200 comprises an extended-area broadband source 201 that is substantially spatially incoherent. In an example, the substantially incoherent broadband source 201 comprises one or more substantially spatially incoherent light emitters 203, e.g., LEDs, such as shown in the close-up view of broadband source 201 of FIG. 24. In other examples, substantially spatially incoherent broadband source 201 includes a filament-based source or a lamp. Also in an example, lens 202 has a focal length based on the size and emission pattern of substantially spatially incoherent broadband source 201.

Figure 24:
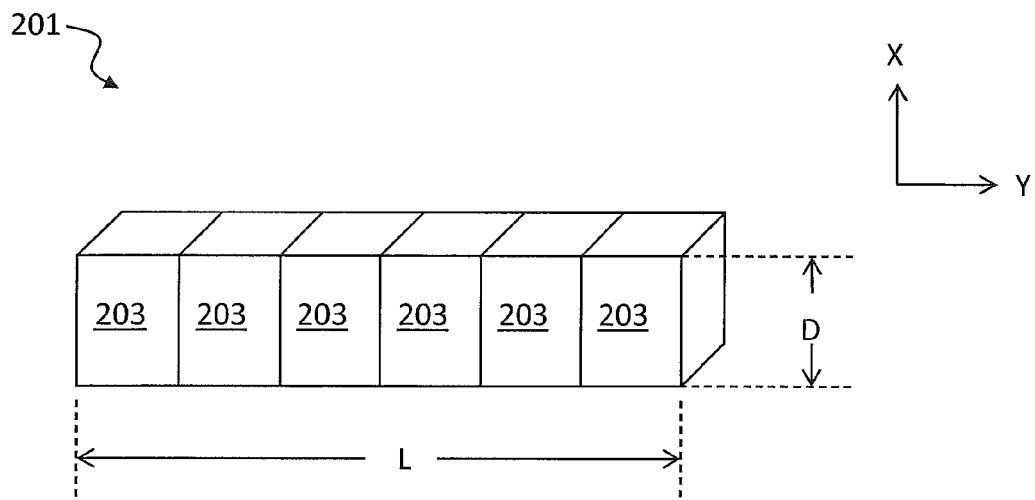
FIG. 24 is a close-up view of an example substantially incoherent broadband source formed as an array of substantially spatially incoherent emitters.
Figure 25:
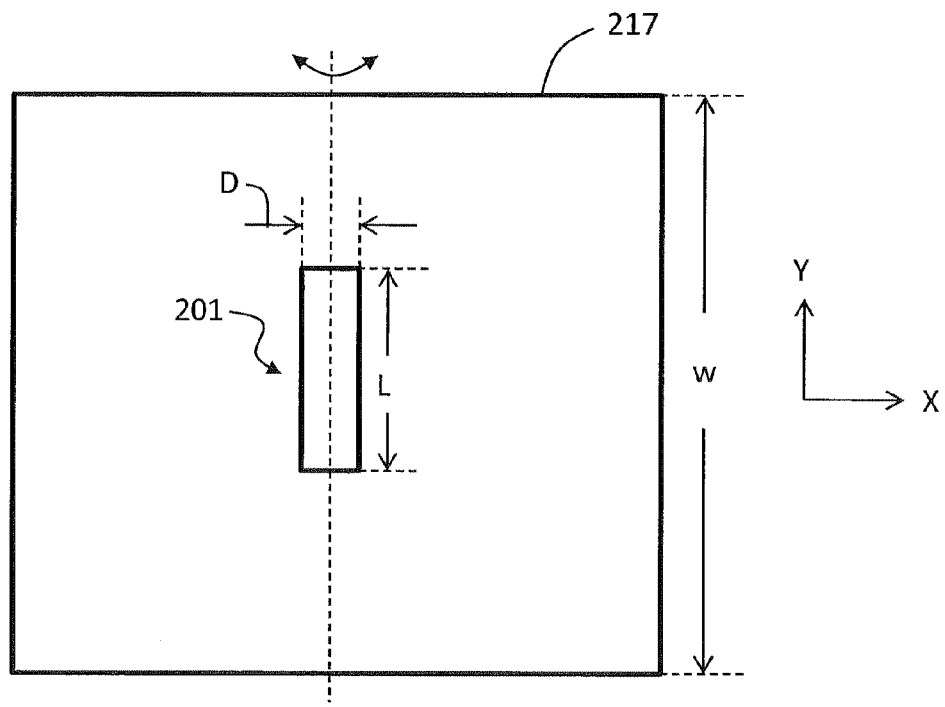
FIG. 25 is a schematic diagram that illustrates the dimensions of an example substantially incoherent broadband light source and an example corresponding rotatable tunable filter.

The use of LEDs as light emitters 203 is advantageous in that LEDs are highly reliable, are relatively low cost, are compact, consume relatively little power, and emit light substantially incoherently over a relatively wide spectral range. Substantially spatially incoherent broadband source 201 can comprise a linear array of light emitters 203 as shown in FIG. 24, or can be configured as a two-dimensional array having various shapes (square, circular, rectangular, etc.). FIG. 25 is a schematic diagram that illustrates the dimensions (length L, width D) of an example substantially spatially incoherent broadband light source 201 and the corresponding filter member 217 of tunable filter 216 of width w. In one example, 2D≦L≦10D, and in a related example, L=8D.

Example substantially spatially incoherent broadband light sources 201 can be formed by packing 0.3×0.3 mm² LED dies to form a one-dimensional LED arrays. Variations on this example include placing a slit aperture (not shown) over one or more large LED emitters, and optically projecting the output of the one or more LEDs to a plane having a slit aperture, thereby creating a virtual elongate source 201. In another example, various geometries for substantially spatially incoherent broadband source 201 can be created using a superluminescent diode and a spinning diffuser (not shown).

Unlike a spatially coherent point source, an extended-area light source cannot be perfectly collimated because different angular components of the light experience different filter functions. There, is thus an additional spectral broadening effect when using substantially spatially incoherent broadband source 201 in tunable light source 106. This angle-induced spectral broadening is desired to be no more than the spectral width $w_f$ of tunable filter 216 for a perfectly collimated beam 210.

In an example, the optimized spectral width of the filtered light beam 134 is about the same as the spectral width of RWG biosensor 102. Therefore, if the angle-induced spectral broadening is equal to the spectral width of tunable filter 216, then the optimum spectral width of the tunable filter is $1/\sqrt{2}$ times that of the resonance width of RWG biosensor 102.

With reference again to FIG. 23 through FIG. 25, an example substantially spatially incoherent broadband source 201 has length L and width D and collimating lens 202 has a focal length f. Filter member 217 has a width w>>D. These source dimensions can be the actual size of source 201 or the size of an optical image of the source.

For f>>D, the (substantially) collimated beam 210 has an angular spread in the x-direction and y-direction of:

$$\Delta_x = \frac{D}{f}$$

$$\Delta_y = \frac{L}{f}$$

The center wavelength of tunable filter 216 depends on the incident angle φ through the relationship:

$$\lambda = \lambda_0 \cos\left(\sin^{-1}\left(\frac{\sin\varphi}{n}\right)\right)$$

where the incident angle spread is:

$$\Delta\phi = \phi_0 - \sqrt{(\phi_0+\Delta_x)^2 + \Delta_y^2}$$

The angular spread in the x-direction $\Delta_x$ has a much larger effect than the angular spread in the y-direction $\Delta_y$.

As an example, assuming a high-refractive-index filter cavity with an effective index n=1.72, the minimum incident angle can be about φ=6° and $\Delta_y$ can be ±2° without significantly impacting the incident angle. To achieve a tuning range from 820 nm to 840 nm, the required maximum incident angle is about φ=22.8°, and the maximum dλ/dφ slope can be as large as 1.8 nm/degree.

The incident-angle spread Δφ in light beam 210 has a more significant impact on the effective filter bandwidth at the short-wavelength end. To reduce this linewidth broadening effect, it is desirable to minimize the x-direction angular spread $\Delta_x$. Having a y-direction angular spread $\Delta_y$ is sufficient to reduce the spatial coherence to an acceptable level. On the other hand, unlike lasers and SLDs, the brightness of other light sources is much lower, and the light emits at substantially all angles (i.e., is substantially Lambertian).

It is thus desirable to have substantially spatially incoherent broadband source 201 with a large emission area (L×D) and to collect large angles of light 210 emitted by the source. An example tradeoff is to have the angle-induced spectral broadening equal to the designed spectral width of tunable filter 216. For example, a total angle spread Δφ=0.5° generates a spectral broadening of 0.9 nm. The angle requirement and the practical size of LED emitters set a minimum focal length f of collimating lens 202. In practice, a low F-number collimating lens 202 is used to maximally collect light 210. This implies a minimum size requirement on filter member 217.

In an exemplary embodiment of the angle tuned filter 216, the filter spectral width $w_f$ is designed to be 1 nm and centered at 838.5 nm at normal incidence. The 1 nm spectral width is close to the optimum value and is practical for manufacturing. The free spectra range tunable filter 216 is more than 100 nm. The tunable filter is diced to a size of 24×18 mm². Center wavelength uniformity is better than 0.1 nm.

Example LED light emitters 203 have a center wavelength of 830 nm and a spectral FWHM of 40 nm. An example dimension of an LED light emitter 203 is 0.3×0.3 mm² and an example emission half angle is 60°. An example LED light emitter 203 has a maximum drive current of 100 mA and a radiant density of about 10 mW/sr.

With reference to FIG. 23, light 210 from LED-based broadband source 201 passes through a polarizer 214 before it is collimated by collimating lens 202 having, for example, a 35 mm focal length f and a 25 mm diameter (i.e., clear aperture). This focal length f is selected by way of example to limit the angular spread Δφ of light beam 210 to less than 0.5°. The LED-based substantially spatially incoherent broadband source 201 is located a focal length f away from collimating lens 202. Substantially collimated light beam 210 passes through polarizer 214 and then through filter member 217. A single-pass configuration is sufficient since the LED light emission is sufficiently spatially uniform.

As discussed above, in one example incident angle is controlled by a galvanometer that responds to a voltage with a slope of 1.2° N. An example tunable filter 216 has an offset angle of φ=11° when V=0.

Figure 26:
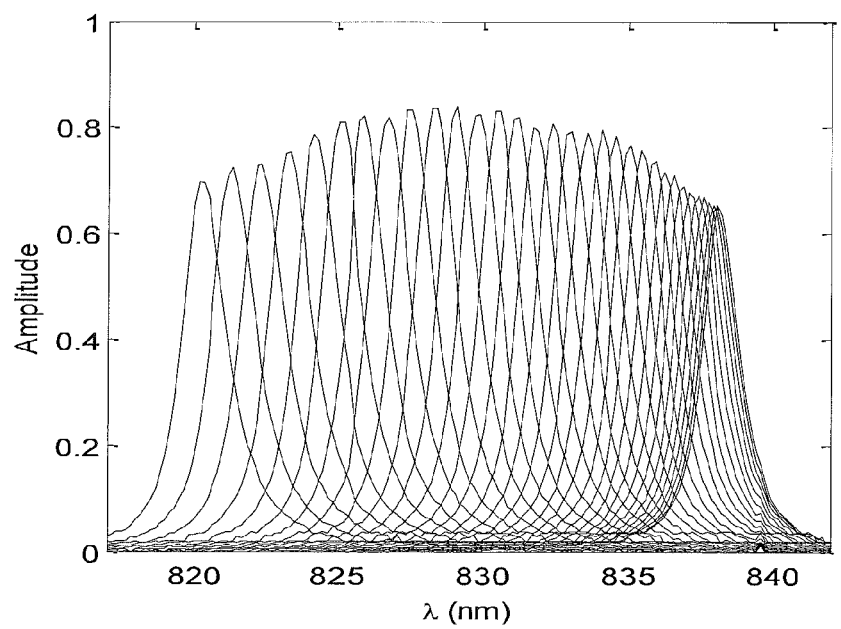
FIG. 26 plots the relative spectral amplitude versus wavelength (nm) of a family of filtered spectra from a tunable light source employing a substantially incoherent broadband source, with the spectra being tuned by over 18 nm with nearly constant amplitude and spectral shape by varying the control voltage of a galvanometer of the tunable filter from −8 V to +8 V.

FIG. 26 plots the relative spectral amplitude versus wavelength (nm) for a family of filtered light beams 134 formed using a tunable light source 106 that employs a substantially spatially incoherent broadband source 201. The spectra are tuned by over 18 nm with nearly consistent amplitude and spectral shape as the control voltage varies from −8 V to +8 V. The spectral width is 1.5 nm at the long-wavelength end and it is slightly broadened to 1.8 nm in the short-wavelength end. This tuning range is sufficient for interrogation of RWG biosensors 102.

Figure 27:
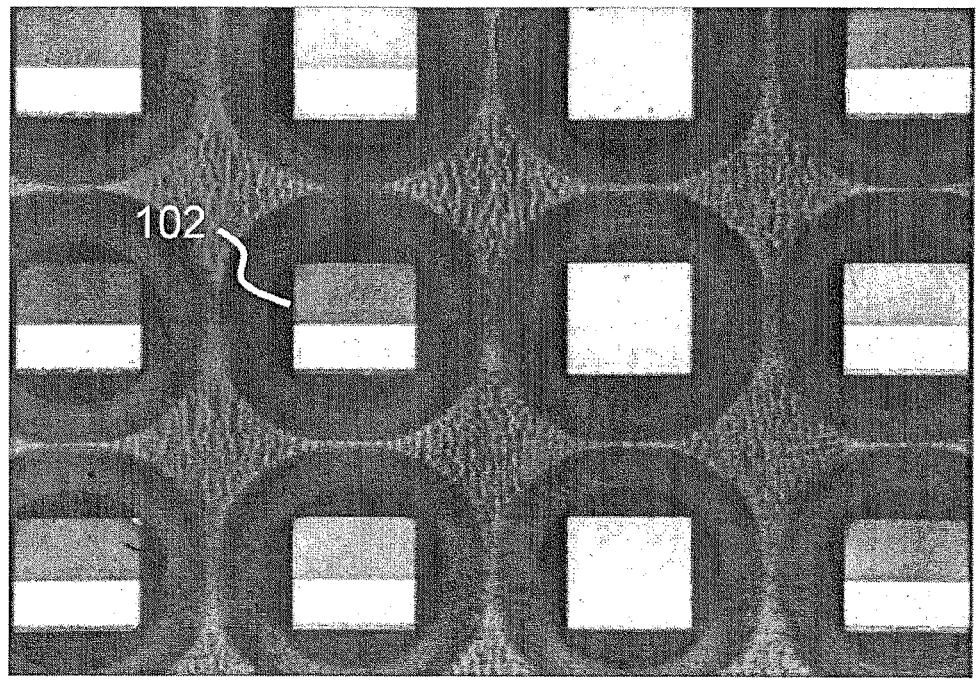
FIG. 27 is a digital image similar to that of FIG. 22, except that the digital image of FIG. 27 was taken using a tunable light source having a substantially spatially incoherent broadband source so that the digital image is free of speckle patterns.

FIG. 27 is similar to FIG. 22, except that the picture of FIG. 27 was taken using a tunable light source 106 have a substantially spatially incoherent broadband source 201. The speckle patterns 302 that were present in FIG. 22 are completely eliminated in FIG. 27, while the spatial uniformity of the illumination is also improved.

Figure 28:
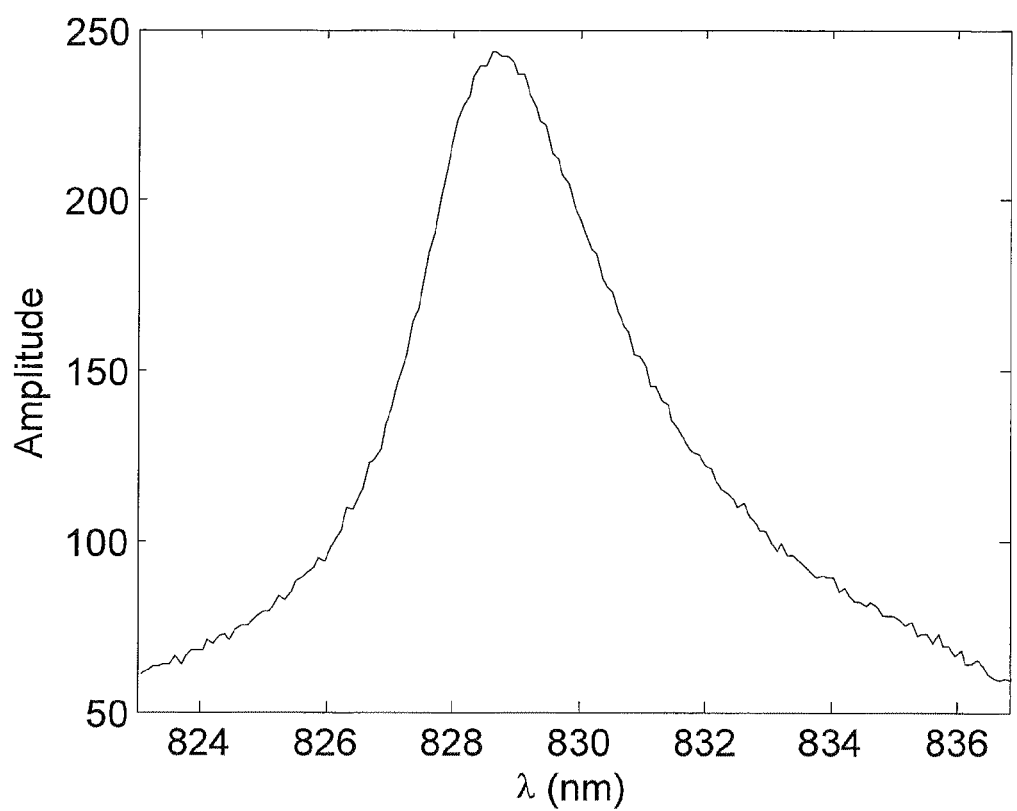
FIG. 28 is a plot of relative amplitude vs. wavelength (nm) for an integrated spectrum for a typical pixel, wherein there is no spectral ripple in the integrated spectrum because of the low temporal and spatial coherence of the tunable light source.

FIG. 28 is a plot of relative amplitude vs. wavelength (nm) for an integrated spectrum for a typical image sensor pixel. The width of the interrogated spectrum in FIG. 28 is widened from about 2 nm (see FIG. 18B) to 3.8 nm. This broadening was also due to the wide-angle spread of interrogation beam 134I incident upon RWG biosensor 102. This broadening can be reduced by expanding interrogation beam 134I. There is no substantially no spectral ripple in the integrated spectrum because of the low temporal and spatial coherence of tunable light source 106.

Optical Interrogation System Using the Tunable Light Source

The tunable light source 106 having a filter spectral linewidth matched to the biosensor resonance linewidth is suitable for use in swept-wavelength optical readers, including photodiode-based multichannel optical readers and CCD/CMOS based imaging optical readers. Tunable light source 106 can replace the narrow-band tunable lasers used in prior art optical reader systems. The measured sensor spectrum is the convolution of the relatively wide spectral linewidth of incident beam 134I and the biosensor resonance linewidth, and this operation automatically removes interference fringes from the sensor.

The simplicity and high performance of tunable light source 106 allows for compact imaging systems 114 and thus enables LID optical reader system 100 to be very compact, i.e., have a small form factor, which in one example is 10 inches by 4 inches by 7 inches. This form factor allows system 100 to fit into a suitcase-sized or briefcase-sized housing, thus making the system easily transportable.

It will be apparent to those skilled in the art that various modifications to preferred embodiments of the disclosure as described herein can be made without departing from the scope of the disclosure as defined in the appended claims. Thus, the disclosure covers the modifications and variations provided they come within the scope of the appended claims and the equivalents thereto.

What is claimed is:

1. A light source for interrogating at least one resonant waveguide grating (RWG) biosensor having a resonance linewidth, comprising:
   a broadband light source that emits a light beam having a first spectral bandwidth greater than the RWG biosensor resonance linewidth;
   a tunable optical filter having a tunable center wavelength and a spectral linewidth and arranged to receive and filter the light beam to cause the light beam to have a second spectral bandwidth substantially the same as the RWG biosensor resonance linewidth; and
   an angle-tuned spectral flattening filter adjacent the tunable optical filter to flatten the first spectral bandwidth of the broadband light source.

2. The light source of claim 1, wherein a central wavelength is tunable as a function of an angle of the tunable optical filter relative to the light beam.

3. The light source of claim 1, wherein the optical filter comprises a single cavity sandwiched by opposing reflective layers.

4. The light source of claim 1, where the optical filter has a free-spectral range (FSR) that is the same as or greater than the first spectral bandwidth.

5. The light source of claim 1, wherein the RWG biosensor resonance linewidth is 0.8 nm measured at full-width half maximum.

6. The light source of claim 1, wherein the broadband light source includes a superluminescent diode (SLD) or a light-emitting diode (LED).

7. The light source of claim 1, wherein the broadband light source comprises a substantially spatially incoherent light source.

8. The light source of claim 7, wherein the broadband light source comprises an array of one or more substantially spatially incoherent light emitters.

9. The light source of claim 8, further comprising the one or more substantially spatially incoherent light emitters comprising one or more LEDs.

10. The light source of claim 1, further comprising:
    a polarizing beam splitter and a quarter-wave plate between the broadband light source and the tunable optical filter, and a fold mirror adjacent the tunable filter opposite the quarter-wave plate, the light beam passes twice through the tunable optical filter and exits the polarizing beam splitter as linearly polarized.

11. A label-independent optical reader for reading at least one resonant waveguide grating (RWG) biosensor supported by a microplate, comprising:
    the light source of claim 1 to emit filtered light beams having wavelengths that sweep over the first spectral bandwidth;
    an illumination system to direct the filtered light beams to the at least one RWG biosensor and form corresponding reflected light beams;
    an optical imager to receive the reflected light beams and form digital images; and
    a controller to process the digital images to establish a resonant wavelength for the at least one RWG biosensor.

12. A label-independent optical reader for reading at least one resonant waveguide grating (RWG) biosensor supported by a microplate, comprising:
    the light source of claim 1 to emit a filtered light beam having a fixed wavelength within the first spectral bandwidth;
    an illumination system to direct the filtered light beam to the at least one RWG biosensor to form a corresponding reflected light beam;
    an optical imager to receive any reflected light beams and form digital images; and
    a controller to process the digital images to translate an intensity change to a resonant wavelength shift for the at least one RWG biosensor.

13. A method of reading at least one resonant waveguide grating (RWG) biosensor having a resonance linewidth, comprising:
    generating a light beam having a first spectral bandwidth greater than the RWG biosensor resonance;
    passing the light beam through a tunable optical filter and an angle-tuned spectral flattening filter adjacent the tunable optical filter to flatten the first spectral bandwidth of the broadband light source, and adjusting the tunable filter to generate a series of light beams each having a second spectral bandwidth substantially the same as the RWG biosensor resonance linewidth but having different central wavelengths within the resonance linewidth;
    directing the series of filtered light beams to be incident the at least one RWG biosensor and to generate a corresponding series of reflected light beams;
    forming a series of digital images of the at least one RWG biosensor based on the series of reflected light beams; and
    processing the series of digital images to establish a resonant wavelength for the at least one RWG biosensor.

14. The method of claim 13, further comprising generating the light beam using one of a superluminous diode (SLD) and a light-emitting diode (LED).

15. The method of claim 13, wherein adjusting the tunable optical filter comprises changing a filter angle relative to the light beam passing therethrough.

16. The method of claim 13, further comprising supporting the tunable filter in a filter support device and adjusting the filter angle by a control signal provided to the filter support device.

17. The method of claim 13, wherein said generating the light beam includes emitting light from a substantially spatially incoherent broadband light source.

18. The method of claim 13, further comprising forming the substantially spatially incoherent broadband light source with one or more light-emitting diodes (LEDs).

19. A method of reading at least one resonant waveguide grating (RWG) biosensor having a resonance linewidth, comprising:
generating a light beam having a first spectral bandwidth greater than the RWG biosensor resonance linewidth;
passing the light beam through a tunable optical filter and adjusting the tunable filter to generate a light beam having a second spectral bandwidth substantially the same as the RWG biosensor resonance linewidth and a fixed central wavelength within the resonance linewidth;
passing the light beam through an angularly tuned flattening filter to flatten the first spectral bandwidth of the broadband light source;
directing the filtered light beam to be incident the at least one RWG biosensor to generate a corresponding reflected light beam;
forming a series of digital images of the at least one RWG bionsensor based on the reflected light beam; and
processing the series of digital images to establish a resonant wavelength for the at least one RWG biosensor.

20. The method of claim 19, wherein adjusting the tunable optical filter further comprises changing a filter angle relative to the light beam passing therethrough.

21. The method of claim 19, wherein processing the series of digital images comprises translating intensity changes into shifts in the resonant wavelength.

22. The method of claim 19, further comprising generating the light beam using one of a superluminous diode (SLD) and a light-emitting diode (LED).

23. The method of claim 19, wherein said generating the light beam includes emitting light from a substantially spatially incoherent broadband light source.

24. The method of claim 19, further comprising forming the substantially spatially incoherent broadband light source with one or more light-emitting diodes (LEDs).

* * * * *

UNITED STATES PATENT AND TRADEMARK OFFICE
CERTIFICATE OF CORRECTION

PATENT NO.         : 8,384,905 B2
APPLICATION NO.    : 12/939606
DATED              : February 26, 2013
INVENTOR(S)        : Qi Wu It is certified that error appears in the above-identified patent and that said Letters Patent is hereby corrected as shown below:

In the Specification

In column 14, line 18, replace "217" with -- 219 --.

In column 14, line 20, replace "217" with -- 219 --.

Signed and Sealed this
Twenty-second Day of October, 2013

Teresa Stanek Rea
*Deputy Director of the United States Patent and Trademark Office*